United States Patent
Lee

(10) Patent No.: US 11,076,769 B2
(45) Date of Patent: Aug. 3, 2021

(54) HUMAN BODY WEARABLE DEVICE AND OPERATION METHOD THEREOF

(71) Applicant: LG Innotek Co., Ltd., Seoul (KR)

(72) Inventor: Sang Hun Lee, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 682 days.

(21) Appl. No.: 15/566,299

(22) PCT Filed: Apr. 12, 2016

(86) PCT No.: PCT/KR2016/003859
§ 371 (c)(1),
(2) Date: Oct. 13, 2017

(87) PCT Pub. No.: WO2016/167552
PCT Pub. Date: Oct. 20, 2016

(65) Prior Publication Data
US 2018/0098708 A1  Apr. 12, 2018

(30) Foreign Application Priority Data

Apr. 14, 2015 (KR) .................. 10-2015-0052742

(51) Int. Cl.
*A61B 5/024* (2006.01)
*A61B 5/1455* (2006.01)
(Continued)

(52) U.S. Cl.
CPC ............ *A61B 5/02438* (2013.01); *A61B 5/00* (2013.01); *A61B 5/1455* (2013.01); *A61B 5/681* (2013.01);
(Continued)

(58) Field of Classification Search
CPC ... A61B 5/02438; A61B 5/1455; A61B 5/681; A61B 5/6843; A61B 5/7221; G06F 1/3231
See application file for complete search history.

(56) References Cited

U.S. PATENT DOCUMENTS 5,782,237 A    7/1998  Casciani et al.
9,442,523 B2 *  9/2016  Lee .................... G06F 1/163
(Continued)

FOREIGN PATENT DOCUMENTS

CN    101108126 A    1/2008
CN    102781310 A    11/2012
(Continued)

OTHER PUBLICATIONS

Colechin et al., "Market review:Pulse oximeters in primary and prehospital care", CEP10066, Mar. 2010 (Year: 2010).*
(Continued)

*Primary Examiner* — Devin B Henson
(74) *Attorney, Agent, or Firm* — Saliwanchik, Lloyd & Eisenschenk

(57) ABSTRACT

According to an embodiment of the present disclosure, there is provided a human body wearable device including: a light emitting unit for generating light to outside, a light receiving unit for receiving light incident from outside; and a control unit for controlling an operation of the light emitting unit and detecting an intensity of light incident on the light receiving unit depending on the operation of the light emitting unit, and detecting a wearing state of the human body wearable device based on an intensity of detected light, wherein the control unit detects the wearing state using a difference value between an intensity of the light incident on the light receiving unit in an ON section of the light emitting
(Continued)

unit and that of the light incident on the light receiving unit in an OFF section of the light emitting unit.

2 Claims, 16 Drawing Sheets

(51) Int. Cl.
    *A61B 5/00*         (2006.01)
    *G06F 3/01*         (2006.01)
    *G06F 1/3231*     (2019.01)
    *A61B 5/11*         (2006.01)
    *H01L 31/167*     (2006.01)

(52) U.S. Cl.
    CPC ............. *G06F 3/011* (2013.01); *A61B 5/1118* (2013.01); *A61B 5/6843* (2013.01); *A61B 5/7221* (2013.01); *G06F 1/3231* (2013.01); *H01L 31/167* (2013.01)

(56) References Cited

U.S. PATENT DOCUMENTS

| | | | |
|---|---|---|---|
| 9,794,653 B2* | 10/2017 | Aumer | G08B 21/18 |
| 10,602,981 B2* | 3/2020 | Karnik | A61B 5/7267 |
| 2006/0202950 A1 | 9/2006 | Lee et al. | |
| 2008/0019218 A1 | 1/2008 | Klopfenstein et al. | |
| 2010/0160794 A1 | 6/2010 | Banet et al. | |
| 2012/0150052 A1 | 6/2012 | Buchheim et al. | |
| 2013/0005310 A1 | 1/2013 | Lim et al. | |
| 2013/0131473 A1 | 5/2013 | Gu et al. | |
| 2014/0073486 A1* | 3/2014 | Ahmed | G16H 20/40 |
| | | | 482/9 |
| 2014/0142403 A1 | 5/2014 | Brumback et al. | |
| 2014/0275854 A1 | 9/2014 | Venkatraman et al. | |
| 2015/0018900 A1 | 1/2015 | Kirk et al. | |
| 2015/0019682 A1 | 1/2015 | Lim | |
| 2015/0374240 A1* | 12/2015 | Lee | A61B 5/4866 |
| | | | 600/483 |

FOREIGN PATENT DOCUMENTS

| | | |
|---|---|---|
| CN | 103156591 A | 6/2013 |
| CN | 104207755 A | 12/2014 |
| CN | 104207761 A | 12/2014 |
| CN | 104245047 A | 12/2014 |
| KR | 10-0537503 B1 | 12/2005 |
| KR | 10-1000467 B1 | 12/2010 |
| KR | 10-1218200 B1 | 1/2013 |
| KR | 10-2013-0043486 A | 4/2013 |
| KR | 10-2015-0009032 A | 1/2015 |

OTHER PUBLICATIONS

Supplementary European Search Report dated Oct. 30, 2018 in European Application No. 16780275.0.
Office Action dated Feb. 3, 2020 in Chinese Application No. 2020012300474760.
International Search Report in International Application No. PCT/KR2016/003859, filed Apr. 12, 2016.

* cited by examiner

PRIOR ART

FIG. 6
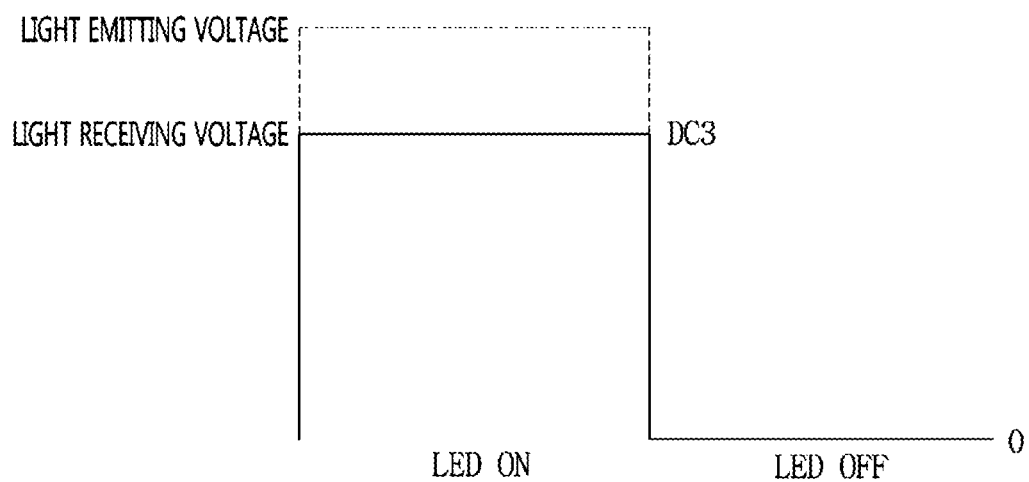
(a)
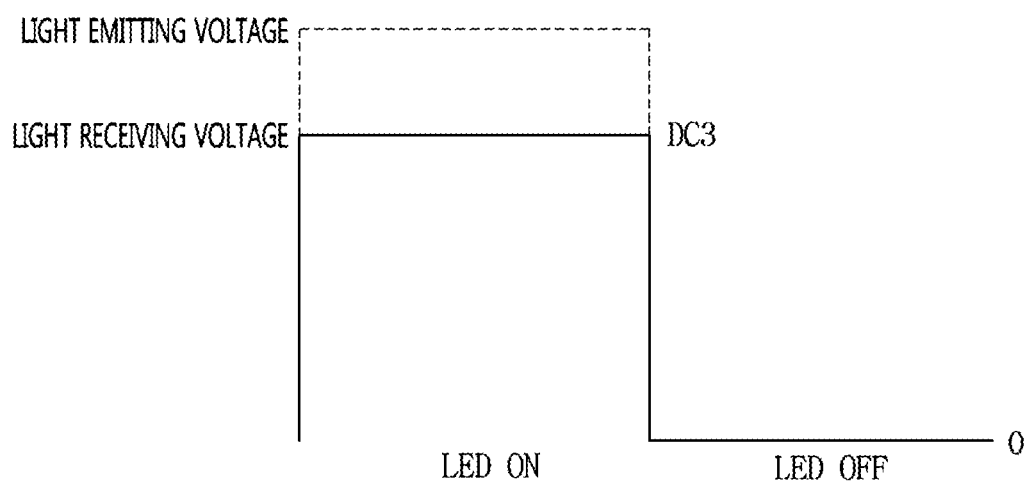
(b)

FIG. 7
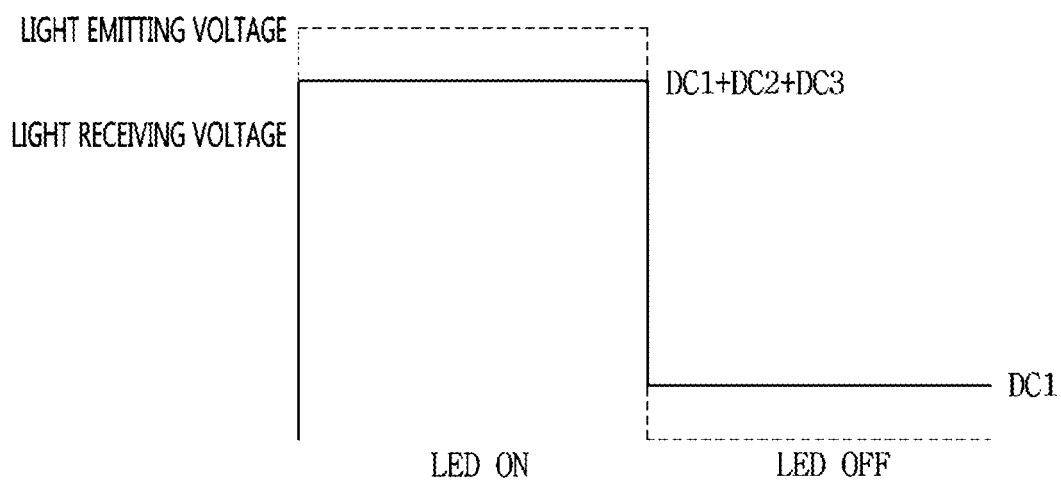
(a)
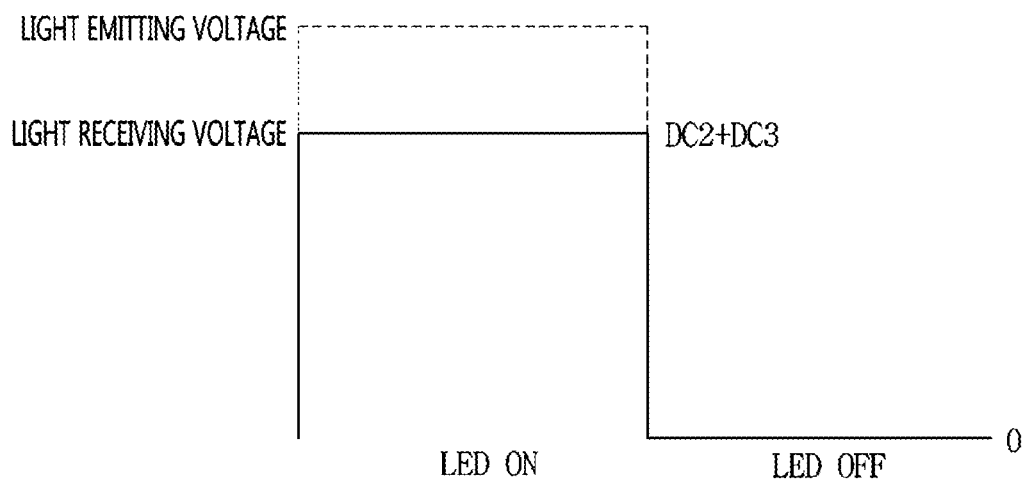
(b)

FIG. 8
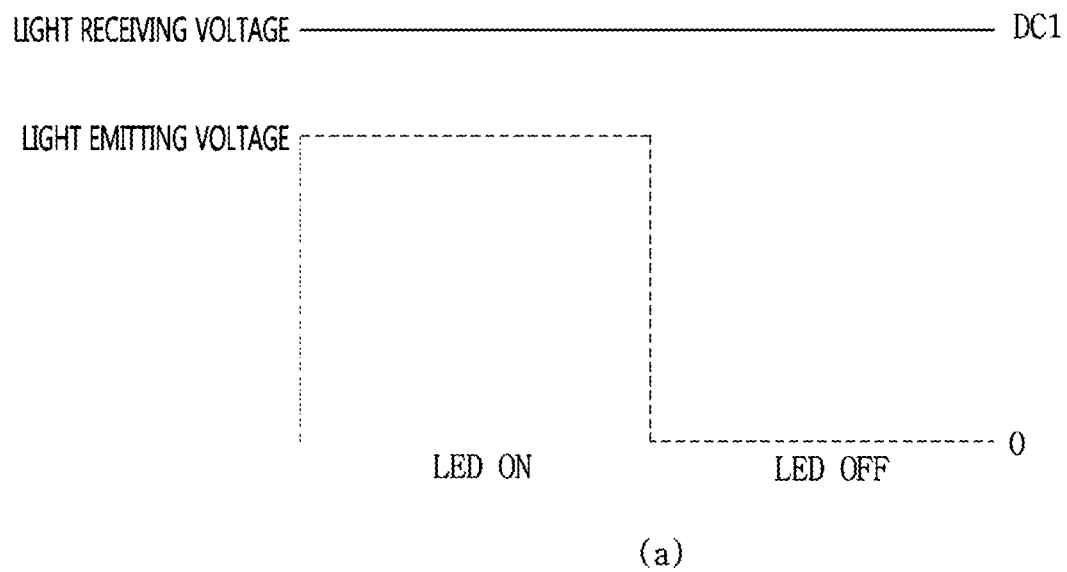
(a)
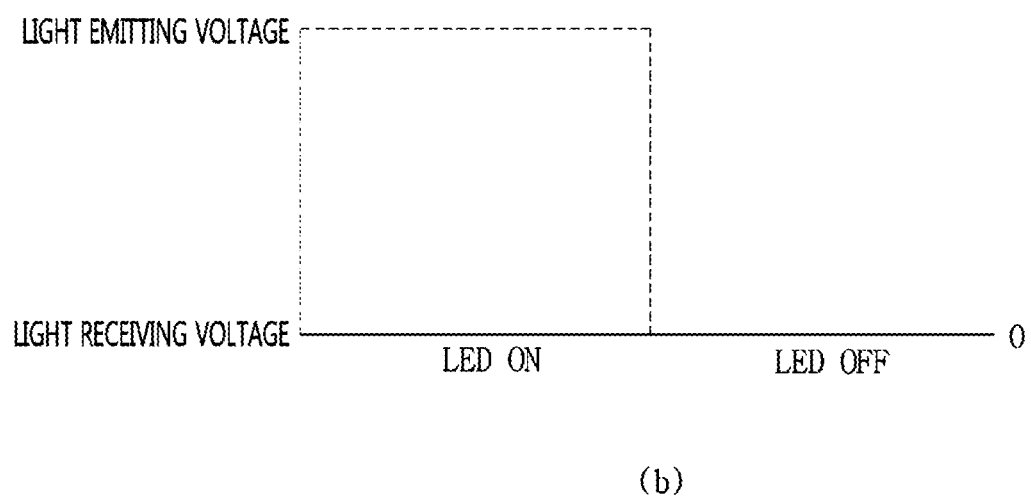
(b)

FIG. 11
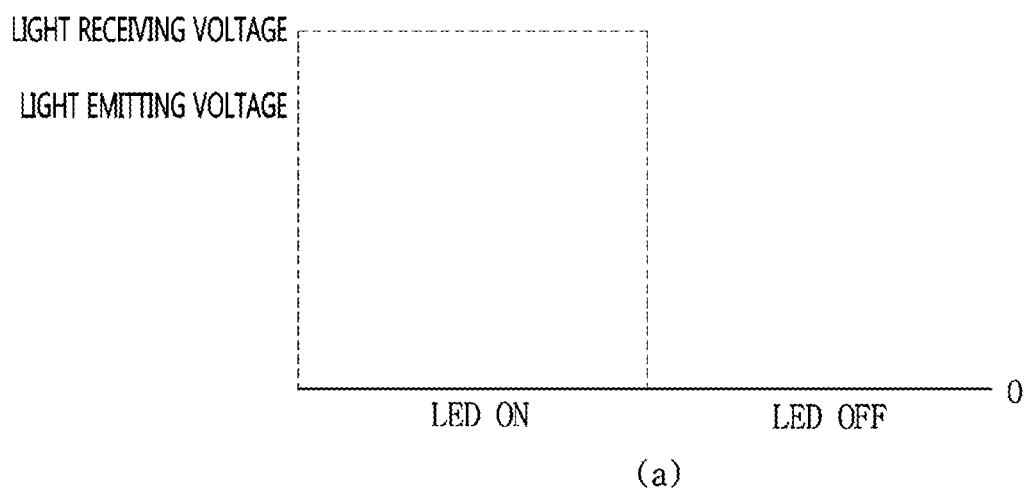
(a)
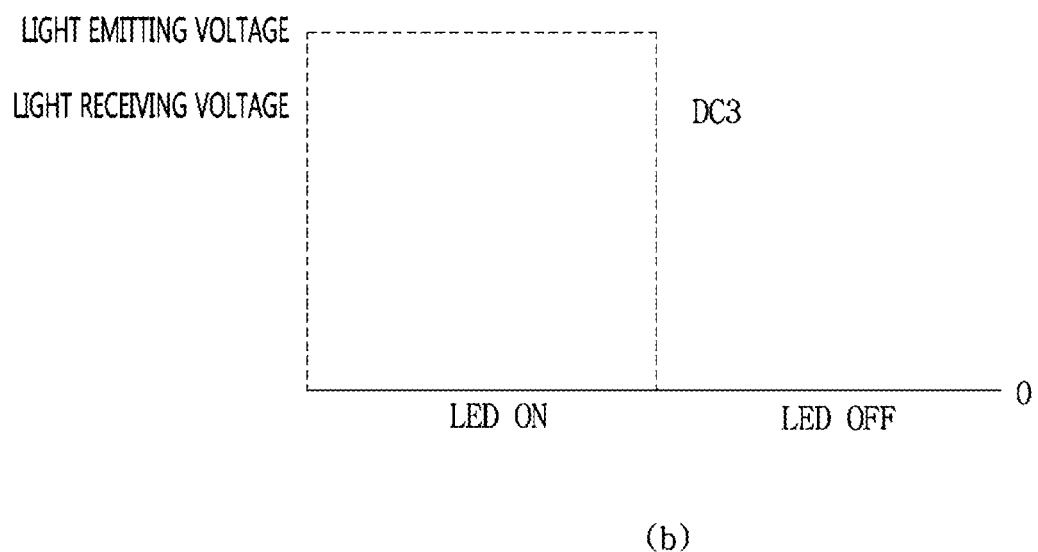
(b)

FIG. 12
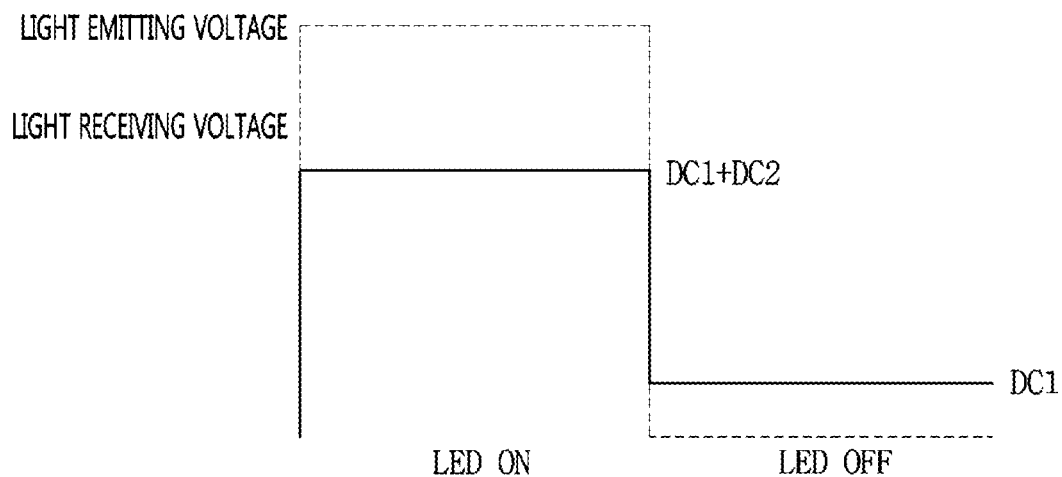
(a)
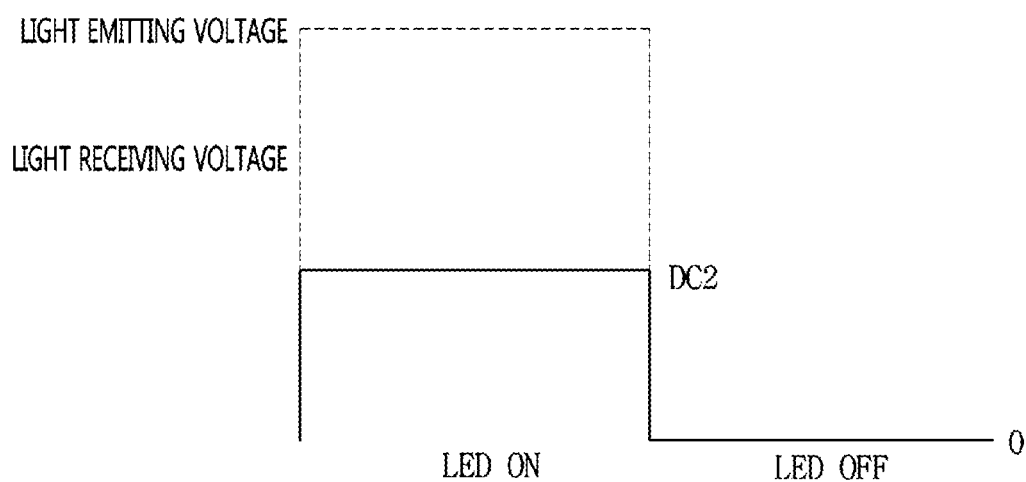
(b)

FIG. 13
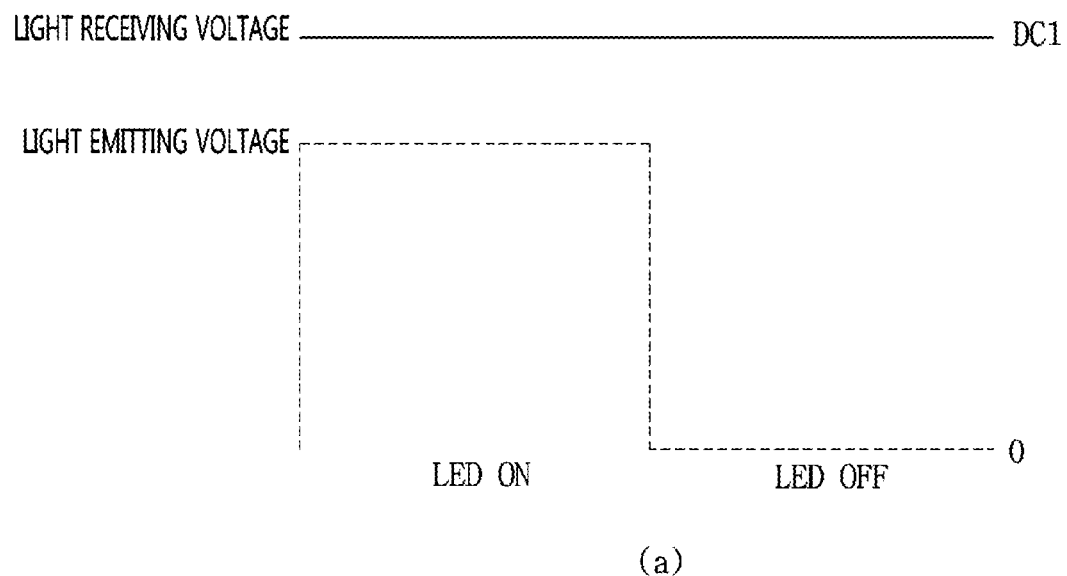
(a)
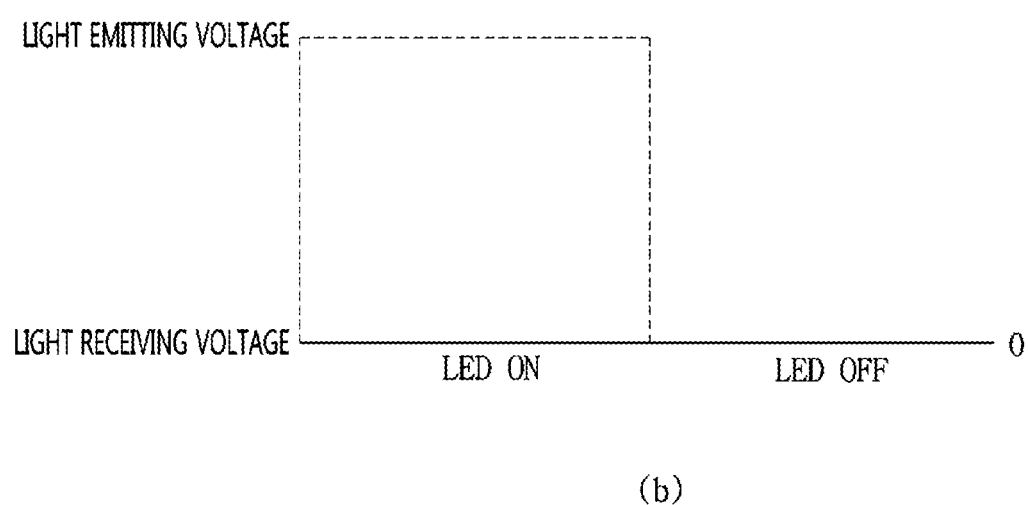
(b)

HUMAN BODY WEARABLE DEVICE AND OPERATION METHOD THEREOF

CROSS-REFERENCE TO RELATED APPLICATIONS

This application is the U.S. national stage application of International Patent Application No. PCT/KR2016/003859, filed Apr. 12, 2016, which claims priority to Korean Application No. 10-2015-0052742, filed Apr. 14, 2015, the disclosures of each of which are incorporated herein by reference in their entirety.

TECHNICAL FIELD

Embodiments relate to a human body wearable device and an operation method thereof.

BACKGROUND ART

Typically, portable terminals are following a trend of high sensitivity, miniaturization and light weight of electronic parts, bar type mobile phones have become universalized as a first generation of mobile terminals, flip type mobile phones have become popularized as a second generation, currently, and a trend of flip type and third generation folder type mobile phones are coexisting and becoming a universalized trend In addition, a wearable device worn on a part of a human body or clothing such as a watch type mobile phone worn on a user's wrist has been developed.

Meanwhile, as the living standard has improved and a medical technology has developed, a trend of aging has become prominent worldwide. In addition, prevalence of chronic diseases is increasing with the population aging. As another problem of aged society, an increasing number of elderly living alone and dying alone caused by declining family support ability due to nuclear family are emerging as an important social issue.

Patients with chronic diseases such as hypertension, diabetes, cerebrovascular disease, heart disease, or the like are continuously increasing. The cause is, in particular, an occurrence of diseases caused by the health behavior of individuals or groups such as diet, exercise, or the like related to health and accounts for almost half or more. Therefore, it is difficult to solve the chronic diseases only by a bio-medical model approach of modern medicine, and a new disease management method, that is, a health promotion approach is required for elimination of health risk factors by improving life habits.

Therefore, recently, pulse rate measuring methods include a piezoelectric type using a piezoelectric element or the like, a magnetic type using a magnetic junction tunnel (MTJ) element, a pressing type using a pressure film sensor, an impedance type using a bioelectrical impedance, an optical type using a light sensor, and the like. Recently, a human-wearable pulse measuring device that can be worn on a wrist or a neck has been proposed.

FIG. 1 is a view illustrating a human body wearable device according to the related art.

Referring to FIG. 1, a human body wearable device includes a substrate 10, a light emitting element 20, a light receiving element 30, a structure 40, a partition wall 50, and an optical window 60.

The substrate 10 is a base substrate for mounting components constituting the human body wearable device.

The light emitting element 20 generates light of a specific wavelength band depending on a light emitting control signal.

The light receiving element 30 receives light incident depending on light generated via the light emitting element 20.

The structure 40 is a support structure for supporting the optical window 60.

The partition wall 50 is disposed between the light emitting element 20 and the light receiving element 30 and prevents light generated via the light emitting element 20 from being directly incident on the light receiving element 30.

The optical window 60 is disposed on a light emitting surface and a light receiving surface of the light emitting element 20 and the light receiving element 30 respectively and protects the light emitting element 20 and the light receiving element 30 from an outside.

The human body wearable device as described above detects a human body signal depending on a light voltage, that is, a light receiving voltage received via the light receiving element 30. Here, the human body signal may include heart rate, oxygen saturation, or the like.

Meanwhile, the human body wearable device as described above is required to detect whether to be worn or not on a human body, and the human body signal is detected depending on a detection result.

In the related art, a method of detecting whether to wear or not the above is as follows.

The light emitting element 20 generates light, and the light receiving element 30 measures a magnitude of a incident photo-current. At this point, when the human body wearable device is worn on a human body, the measured photo-current includes relatively low ambient light, and when the human body wearable device is not worn on the human body, the measured photo-current includes high ambient light.

That is, in a state in which the human body wearable device is worn by a human body, since a test object and the human body wearable device are brought into close contact with each other and an introduction path of ambient light is substantially blocked, a weak photo-current is detected. In contrast, in a state in which the human body wearable device is not worn by a human body, as a separation distance between the test object and the human body wearable device increases, a large photo-current is detected due to exposure to ambient light.

Therefore, the human body wearable device detects whether the human body wearable device has been worn or not by the human body depending on a magnitude of the photo-current detected through the light receiving element 30.

FIG. 2 is a graph illustrating a condition for detecting whether to wear or not a human body wearable device according to the related art.

Referring to FIG. 2, as a separation distance between a human body wearable device and a test object (preferably a human body) increases, a magnitude of the light receiving voltage detected via the light receiving element 30 increases.

Therefore, a human body wearable device determines a reference value (V TH) in a state in which the human body wearable device is not worn, and when a magnitude of the light receiving voltage is smaller than that of the reference value, the human body wearable device detects a state in which the human body wearable device is worn on a human body. On the other hand, when a magnitude of the light receiving voltage is greater than that of the reference value (V TH), the human body wearable device detects a state in which the human body wearable device is not worn on the human body.

However, the method of detecting whether to wear or not according to the related art as shown above has problems as follows.

As a method of detecting whether to wear or not as described above, it is possible to classify a wearing state of the human body wearable device during daytime or in a bright place due to lighting, but there is a problem in a night time or dark place that a photo-current due to ambient light is weak, so that an accurate wearing state is not detected.

In addition, since the photo-current due to the ambient light is weak even in a state in which the human body wearable device is in contact with a thing, not a human, as a method of detecting whether or not to wear as described above, even in a state in which the human body wearable device is not substantially worn on the human body, there is a problem in which a malfunction that the human body wearable device is worn on the human body occurs.

DISCLOSURE

Technical Problem

In an embodiment, a human body wearable device capable of detecting an accurate wearing state of a human body wearable device without being affected by an external environment and a method of operating the same are provided.

In addition, in an embodiment, a human body wearable device capable of discriminating whether a human body wearable device is worn on a human body or in contact with a thing, and a method of operating the same are provided.

Technical problems to be solved by the embodiments proposed herein are not limited to those mentioned above, and other unmentioned technical aspects should be clearly understood by one of ordinary skill in the art to which the embodiments proposed herein pertain from the description below.

Technical Solution

According to an embodiment of the present disclosure, there is provided a human body wearable device including: a light emitting unit for generating light to outside; a light receiving unit for receiving light incident from outside; and a control unit for controlling an operation of the light emitting unit and detecting an intensity of light incident on the light receiving unit depending on the operation of the light emitting unit, and detecting a wearing state of the human body wearable device based on an intensity of detected light, wherein the control unit detects the wearing state using a difference value between an intensity of light incident on the light receiving unit in an ON section of the light emitting unit and that of light incident on the light receiving unit in an OFF section of the light emitting unit.

In addition, if the difference value is zero, the control unit detects a state of the human body wearable device as a non-wearing state, and if the difference value is greater than zero, the control unit detect the state of the human body wearable device as the wearing state.

Further, if the difference value is greater than a predetermined reference value, the control unit detects the state of the human body wearable device as the wearing state, and if the difference value is less than or equal to the predetermined reference value, the control unit detect the state of the human body wearable device as the non-wearing state.

Furthermore, the reference value is determined by at least one of a direct light leakage amount from the light emitting unit to the light receiving unit and a light reflection amount by an external environment.

In addition, the light emitting unit includes a first light emitting unit for generating light of a first wavelength and a second light emitting unit for generating light of a second wavelength different from the first wavelength. The control unit detects the wearing state by using any one of the light emitting units of the first light emitting unit and the second light emitting unit and detects heart rate and blood oxygen saturation by using both the first light emitting unit and the second light emitting unit.

Further, the light emitting unit includes a first light emitting unit for generating first light and a second light emitting unit for generating second light. The light receiving unit includes a first light receiving unit for receiving light incident from outside depending on an operation of the first light emitting unit, and a second light receiving unit for receiving light incident from outside depending on an operation of the second light emitting unit.

Furthermore, the first light emitting unit and the first light receiving unit operate at a predetermined cycle depending on a control signal of the control unit to detect a wearing state of the human body wearable device, and the second light emitting unit and the second light receiving unit detect a human body signal for a human body on which the human body wearable device is worn depending on a control signal of the control unit.

In addition, when the control unit detects the state of the human body wearable device as the wearing state, the control unit detects an object on which the human body wearable device is worn based on an intensity of light received through the light receiving unit in the ON section of the light emitting unit.

Further, the control unit detects a raw signal waveform of a pulse wave by using an intensity of light received through the light receiving unit in the ON section of the light emitting unit, generates a waveform of a secondary differential signal by secondarily differentiating the detected raw signal waveform of the pulse wave, generates a peak signal waveform by detecting a peak signal from the generated second-order differential signal waveform, and determines an object on which the human body wearable device is worn based on a heart rate (HR) of the peak signals included in the generated peak signal waveform.

In addition, if the heart rate (HR) is within a range of 30 to 240 bpm, the control unit determines the human body wearable device which is worn on a human body, and if the heart rate (HR) exceeds the range of 30 to 240 bpm, the control unit determines the human body wearable device which is worn on a thing.

Further, the control unit includes a display unit for displaying at least one of wearing state information of the human body wearable device and a human body detection signal detected from a human body wearing the human body wearable device depending on a control signal of the control unit.

Meanwhile, a method of operating a human body wearable device according to an embodiment includes outputting a pulse signal including ON and OFF sections; operating a light emitting unit depending on the pulse signal; detecting an intensity of light incident on a light receiving unit in the ON section and an intensity of light incident on the light receiving unit in the OFF section; detecting a difference value between an intensity of the light in the ON section and an intensity of the light in the OFF section; and determining whether or not the human body wearable device is worn on an object based on the difference value.

In addition, the step of determining whether to be worn or not on the object includes determining a state of the human body wearable device as a non-wearing state if the difference value is zero, and determining the state of the human body wearable device as a wearing state if the difference value is greater than zero.

In addition, the step of determining whether to be worn or not on the object includes determining the state of the human body wearable device as the wearing state if the difference value is greater than a predetermined reference value, and determining the state of the human body wearable device as the non-wearing state if the difference value is smaller or equal to the predetermined reference value.

Furthermore, the reference value is determined by at least one of a direct light leakage amount from the light emitting unit to the light receiving unit and a light reflection amount by an external environment.

In addition, the light emitting unit includes a first light emitting unit for generating light of a first wavelength and a second light emitting unit for generating light of a second wavelength different from the first wavelength. The determination as to whether to wear the above is determined by light emitting of any one of the first light emitting unit and the second light emitting unit.

Further, the light emitting unit includes a first light emitting unit for generating first light and a second light emitting unit for generating second light. The light receiving unit includes a first light receiving unit for receiving light incident from outside depending on an operation of the first light emitting unit, and a second light receiving unit for receiving light incident from outside depending on an operation of the second light emitting unit. The determination as to whether to wear the above is determined by operations of the first light emitting unit and the first light receiving unit.

In addition, when the state of the human body wearable device is detected as the wearing state, the method of operating the human body wearable device further includes: determining whether the object on which the human body wearable device is worn is a human body based on an intensity of light received through the light receiving unit in the ON section.

Further, the step of determining whether the object is a human body includes detecting a raw signal waveform of a pulse wave by using an intensity of light received through the light receiving unit in the ON section of the light emitting unit, generating a waveform of a secondary differential signal by secondarily differentiating the detected raw signal waveform of the pulse wave, generating a peak signal waveform by detecting a peak signal from the generated second-order differential signal waveform, and determining whether the object on which the human body wearable device is worn is a human body based on a heart rate (HR) of the peak signals included in the generated peak signal waveform.

In addition, the step of determining whether the object is a human body includes determining the human body wearable device which is worn on a human body if the heart rate (HR) is within a range of 30 to 240 bpm, and determining the human body wearable device which is worn on a thing if the heart rate (HR) exceeds the range of 30 to 240 bpm.

Further, the method of operating the human body wearable device further includes displaying at least one of wearing state information of the human body wearable device and a human body detection signal detected from a human body wearing the human body wearable device.

Advantageous Effects

According to an embodiment of the present disclosure, it is possible to accurately detect whether the human body wearable device is worn on a human body regardless of daytime or a bright place due to lighting, and a night time or a dark place.

In addition, according to an embodiment of the present disclosure, it is possible to precisely distinguish when the human body wearable device is in contact with a thing other than the human body and to prevent various malfunctions that may occur when the human body wearable device is brought into contact with the thing.

DESCRIPTION OF DRAWINGS

FIG. 6 illustrates a state of a light emitting unit and a light receiving unit in a state in which a human body wearable device according to an embodiment is in complete contact with a human body.

FIG. 7 illustrates a state of a light emitting unit and a light receiving unit in a state in which a human body wearable device according to an embodiment is separated from a human body by a first distance.

FIG. 8 illustrates a state of a light emitting unit and a light receiving unit in a state in which a human body wearable device according to an embodiment is completely separated from a human body.

FIG. 11 illustrates a state of a light emitting unit and a light receiving unit when a human body wearable device according to an embodiment is worn in a state in which the human body wearable device is completely in close contact with a thing.

FIG. 12 illustrates a state of a light emitting unit and a light receiving unit when a human body wearable device according to an embodiment is disposed at a position separated from a thing by a first distance.

FIG. 13 illustrates a state of a light emitting unit and a light receiving unit in a state in which a human body wearable device according to an embodiment is completely separated from a thing.

MODES OF THE INVENTION

Figure 1:
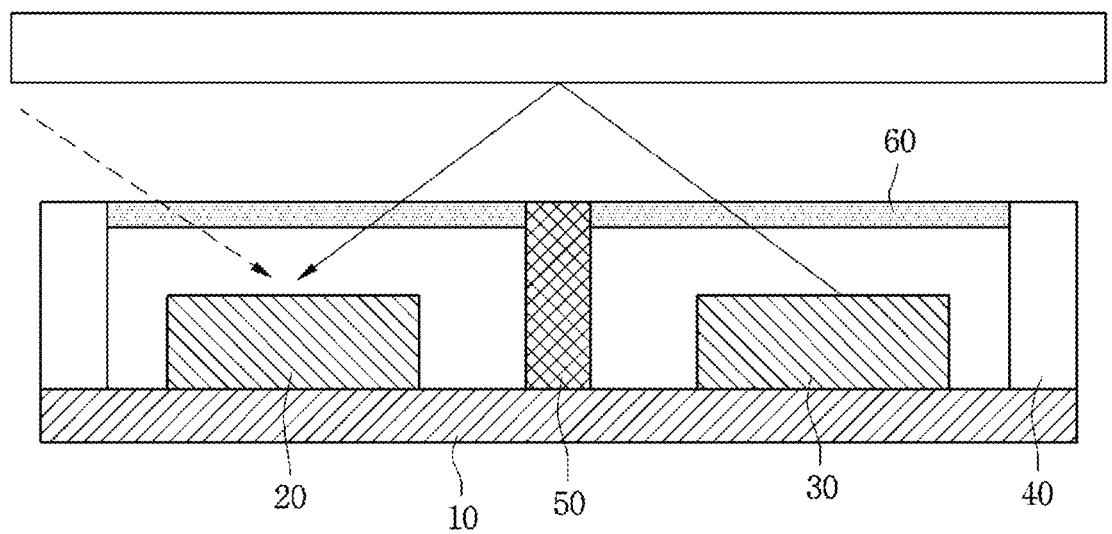
FIG. 1 is a view illustrating a human body wearable device according to the related art.
Figure 2:
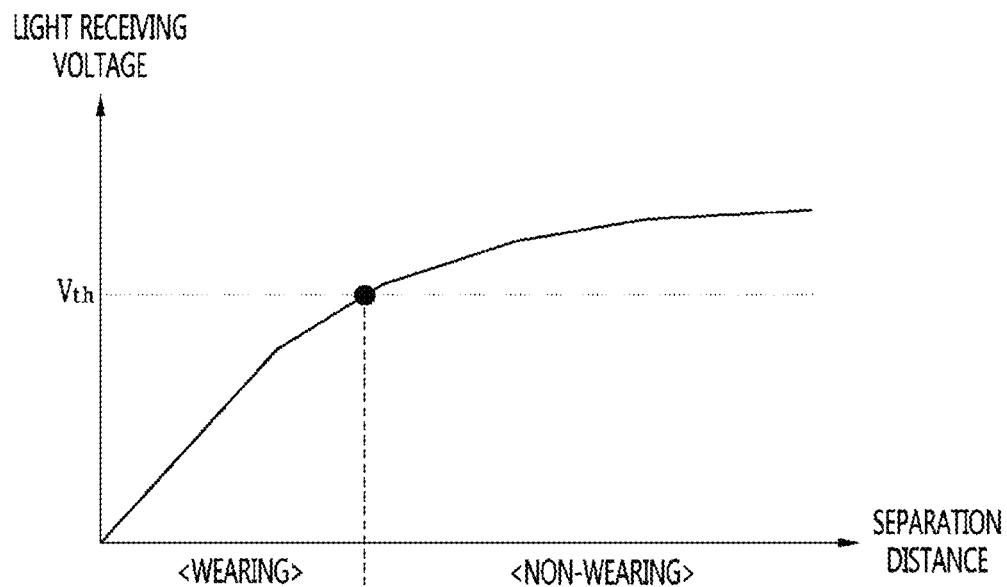
FIG. 2 is a graph illustrating a condition for detecting whether or not to wearing a human body wearable device according to the related art.

Advantages, features, and methods of achieving the same of the present disclosure will become clear upon referring to embodiments described below in detail with reference to the accompanying drawings. However, the present disclosure is not limited to the embodiments disclosed below and may be implemented in various other forms. The embodiments are merely provided to make the disclosure of the present disclosure complete and completely inform one of ordinary skill in the art to which the present disclosure pertains of the scope of the present disclosure. The present disclosure is defined only by the scope of the claims below. Like reference numerals refer to like elements throughout.

In describing embodiments of the present disclosure, when detailed description of a known function or configuration is deemed to unnecessarily blur the gist of the present disclosure, the detailed description will be omitted. Terms described below are terms defined in consideration of functions in the embodiments of the present disclosure and may vary depending on the intention of a user or operator or a practice. Therefore, such terms should be defined on the basis of the entire contents disclosed herein.

Combinations of blocks and steps of flowcharts in the accompanying drawings can be performed by computer program instructions. Such computer program instructions can be embedded in a processor of a general-purpose computer, a special-purpose computer, or other programmable data processing equipment. Therefore, the instructions performed by the processor of other programmable data processing equipment generate means for performing functions described in each of the blocks or each of the steps in the flowcharts in the drawings. Because the computer program instructions can also be saved in a computer-usable or computer-readable memory capable of supporting a computer or other programmable data processing equipment to implement a function in a specific way, the instructions stored in the computer-usable or computer-readable memory can also produce a manufacturing item which incorporates an instruction means performing a function described in each of the blocks or each of the steps of the flowcharts in the drawings. Because the computer program instructions can also be embedded in a computer or other programmable data processing equipment, the instructions performed in a computer or other programmable data processing equipment by a process performed in a computer being generated by a series of operation steps being performed in the computer or other programmable data processing equipment can also provide steps for executing functions described in each of the blocks and each of the steps of the flowcharts in the drawings.

Each of the blocks or each of the steps may represent a module, a segment, or a part of a code including one or more executable instructions for executing a specified logical function(s). Also, it should be noted that functions mentioned in the blocks or steps can also be performed in a different order in a few alternative embodiments. For example, two blocks or steps which are consecutively illustrated can substantially be performed simultaneously, or the blocks or steps can also be performed in a reverse order sometimes according to corresponding functions.

Figure 3:
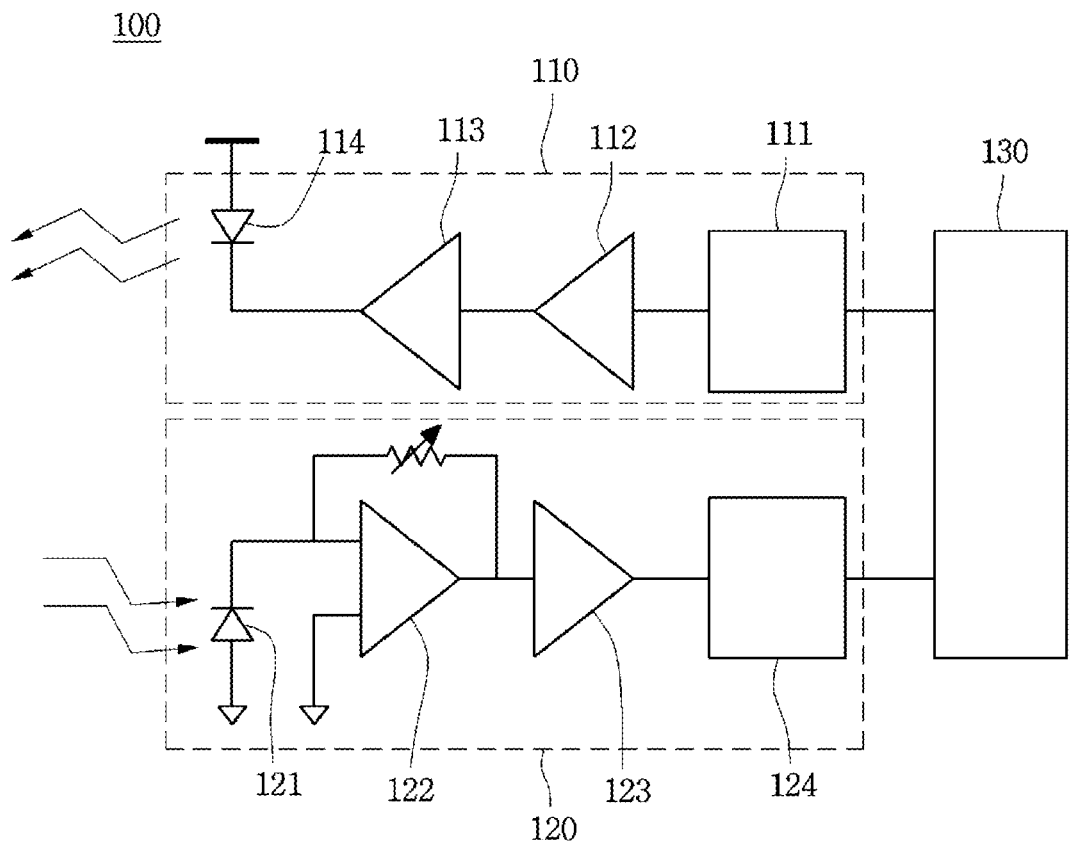
FIG. 3 is a schematic view illustrating a configuration of a human body wearable device according to a first embodiment of the present disclosure.
Figure 4:
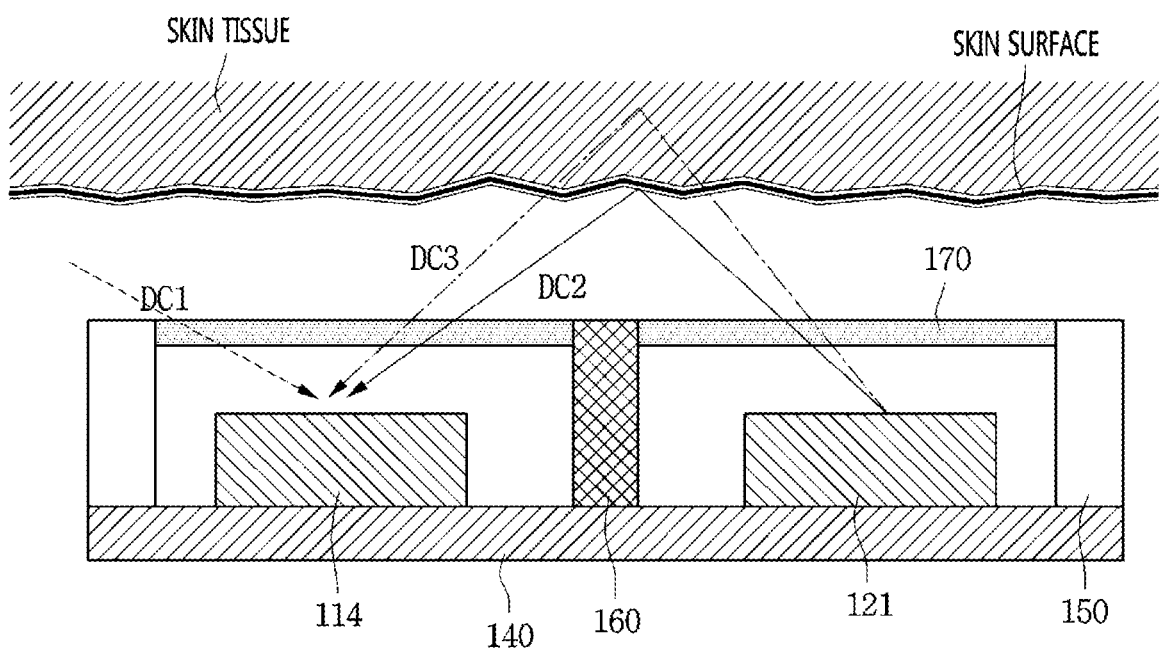
FIG. 4 is a cross-sectional view illustrating a structure of a human body wearable device according to a first embodiment of the present disclosure.

FIG. 3 is a schematic view illustrating a configuration of a human body wearable device according to a first embodiment of the present disclosure, and FIG. 4 is a cross-sectional view illustrating a structure of the human body wearable device according to the first embodiment of the present disclosure.

Referring to FIG. 3, a human body wearable device 100 includes a light emitting unit 110, a light receiving unit 120 and a control unit 130.

The light emitting unit 110 generates light depending on a control signal of the control unit 130.

The light emitting unit 110 may be roughly divided into a light emitting part for generating light and a driving part for driving the light emitting part.

The driving part of the light emitting unit 110 includes: a digital-analog converter 111 for converting a digital signal output via the control unit 130 into an analog signal, a first amplifier 112 for primarily amplifying the signal converted via the digital-analog converter 111, and a second amplifier 113 for secondarily amplifying the signal primarily amplified via the first amplifier 112.

Here, the digital-analog converter 111 converts the digital signal into an analog signal in order to set a current of a light emitting element 114.

Further, the first amplifier 112 and the second amplifier 113 are signal amplifying units for supplying an alternating current necessary for driving the light emitting element 114 to the light emitting element 114.

Furthermore, the light emitting part of the light emitting unit 110 includes a light emitting element 114 for generating light depending on a signal amplified via the second amplifier 113. The light emitting element 114 may be implemented with a light emitting diode (LED).

In addition, the light emitting element 114 may generate light having different wavelengths depending on a human body signal to be detected. That is, the light emitting element 114 may be a red light emitting diode, which generates light having a wavelength of 660 nm when the human body signal to be detected is a heart rate.

The light receiving unit 120 receives incident light including light reflected from a test object depending on a light emitting operation of the light emitting unit 110.

The light receiving unit 120 includes a light receiving element 121 for receiving the incident light, a first amplifier 122 for primarily amplifying an optical signal incident via the light receiving element 121, a second amplifier 123 for secondarily amplifying a signal primarily amplified via the first amplifier 122, and an analog-digital converter 124 for converting a signal secondarily amplified via the second amplifier 123 into a digital signal.

The light receiving element 121 receives light incident from outside. At this point, the light receiving element 121 may be implemented with a photodiode (PD) or a transistor (TR).

In addition, the first amplifier 122 converts a weak photocurrent detected by the light receiving element 121 into a voltage and amplifies the voltage, and the first amplifier 122 may be a trans impedance amplifier (TIA).

Further, the second amplifier 123 amplifies a voltage amplified via the first amplifier 122 to a voltage of sufficient magnitude to be processed by the analog-digital converter 124.

Furthermore, the analog-digital converter 124 converts an analog voltage to an equivalent digital voltage according to a specified sampling rate.

The control unit 130 controls operations of the light emitting unit 110 and the light receiving unit 120.

In addition, the control unit 130 detects a magnitude of an optical signal received via the light receiving unit 120 depending on operation modes of the light emitting unit 110 and the light receiving unit 120 and performs an operation depending on an intensity of the detected optical signal.

At this point, the operation mode includes a wearing state detection mode and a human body signal detection mode.

The wearing state detection mode is a mode for detecting whether the human body wearable device 100 is worn on a human body by using the light emitting unit 110 and the light receiving unit 120.

The human body signal detection mode is a mode for detecting a human body signal with respect to a human body on which the human body wearable device 100 is worn by using the light emitting unit 110 and the light receiving unit 120.

The human body signal detection mode is a mode in which the human body wearable device 100 is performed in a state in which the human body wearable device 100 is worn on a human body.

In addition, the wearing state detection mode is a mode performed at every predetermined cycle, and a mode for detecting whether the human body wearable device 100 is worn on a human body or whether the human body wearable device 100 previously worn is separated from the human body.

The control unit 130 performs an operation corresponding to a intensity of light received via the light receiving unit 120 depending on the determined mode.

In particular, when a wearing state detection mode is entered, the control unit 130 causes light to be generated via the light emitting unit 110, and determines whether the human body wearable device 100 is in a state in which the human body wearable device 100 is worn on a test object depending on an intensity of light received via the light receiving unit 120.

Here, the state in which the human body wearable device 100 is worn on the test object includes both the state in which the human body wearable device 100 is worn on a human body and the state in which the human body wearable device 100 is in contact with a thing.

Accordingly, if the human body wearable device 100 is determined to be in a state in which the human body wearable device 100 is worn on a test object, the control unit 130 determines whether or not the human body wearable device 100 is worn on a human body or simply contacted with a thing.

If the human body wearable device 100 is determined to be worn on a human body, the control unit 130 controls the light emitting unit 110 and the light receiving unit 120 to operate in the human body signal detection mode and to detect a human body signal corresponding to an intensity of a received optical signal accordingly.

Meanwhile, referring to FIG. 4, a structure of the human body wearable device 100 includes a substrate 140, a light emitting element 114, a light receiving element 121, a structure 150, a partition wall 160, and an optical window 170.

The substrate 140 is a base substrate for mounting components constituting the human body wearable device.

The light emitting element 114 generates light of a specific wavelength band depending on a light emitting control signal.

The light receiving element 121 receives light incident depending on light generated via the light emitting element 114.

The structure 150 is a support structure for supporting the optical window 170.

The partition wall 160 is disposed between the light emitting element 114 and the light receiving element 121 and prevents light generated via the light emitting element 114 from being directly incident on the light receiving element 121.

The optical window 170 is spaced apart from a light emitting surface and a light receiving surface of the light emitting element 114 and the light receiving element 121 and protects the light emitting element 114 and the light receiving element 121 from outside.

In addition, the optical window 170 forms a light path so that light generated through the light emitting element 114 is supplied to outside. Further, the optical window 170 allows light incident from the outside to be supplied to the light receiving element 121.

At this point, the light receiving element 121 receives light incident from the outside, and the light is largely composed of three lights.

In other words, the light received via the light receiving unit 120 includes at least one of first light DC1, second light DC2, and third light DC3.

The first light DC1 refers to light incident on the light receiving unit 120 depending on external ambient light regardless of an operation of the light emitting unit 110.

The second light DC2 refers to light which is generated by the light emitting unit 110, is reflected by a surface of a test object, and is incident on the light receiving unit 120 depending on light reflected from the surface.

The third light DC3 refers to light which is generated by the light emitting unit 110, is reflected by a skin tissue of a test object (a human body), and is incident on the light receiving unit 120 depending on light reflected from the skin tissue.

At this point, whether or not the first to third lights are incident on the light receiving unit 120 is determined by a separation distance between the human body wearable device 100 and the test object.

The separation distance refers to a distance between a surface of the human body wearable device 100, that is, the optical window 170 and a surface of the test object, and is determined by a wearing state of the human body wearable device 100.

The wearing state of the human body wearable device 100 includes first, second and third states.

The first state refers to a state in which the human body wearable device 100 is in complete contact with the test object.

The second state refers to a state in which the human body wearable device 100 and the test object are spaced apart from each other by a first distance.

The third state refers to a state in which the human body wearable device 100 is completely separated from the test object, that is, a state in which the human body wearable device 100 is not worn on the test object.

That is, the third state refers to a state in which a distance between the human body wearable device 100 and the test object is separated by a second distance which is greater than the first distance.

In other words, in general, when a user of the human body wearable device 100 wears the human body wearable device 100 on the user's wrist, in order to minimize inconvenience in use, the human body wearable device 100 is worn spaced apart from the wrist by a certain gap.

Therefore, in an embodiment, when the separation distance is within the first distance, the human body wearable device 100 is determined to be in a state in which the human body wearable device 100 is worn on the test object.

Figure 5:
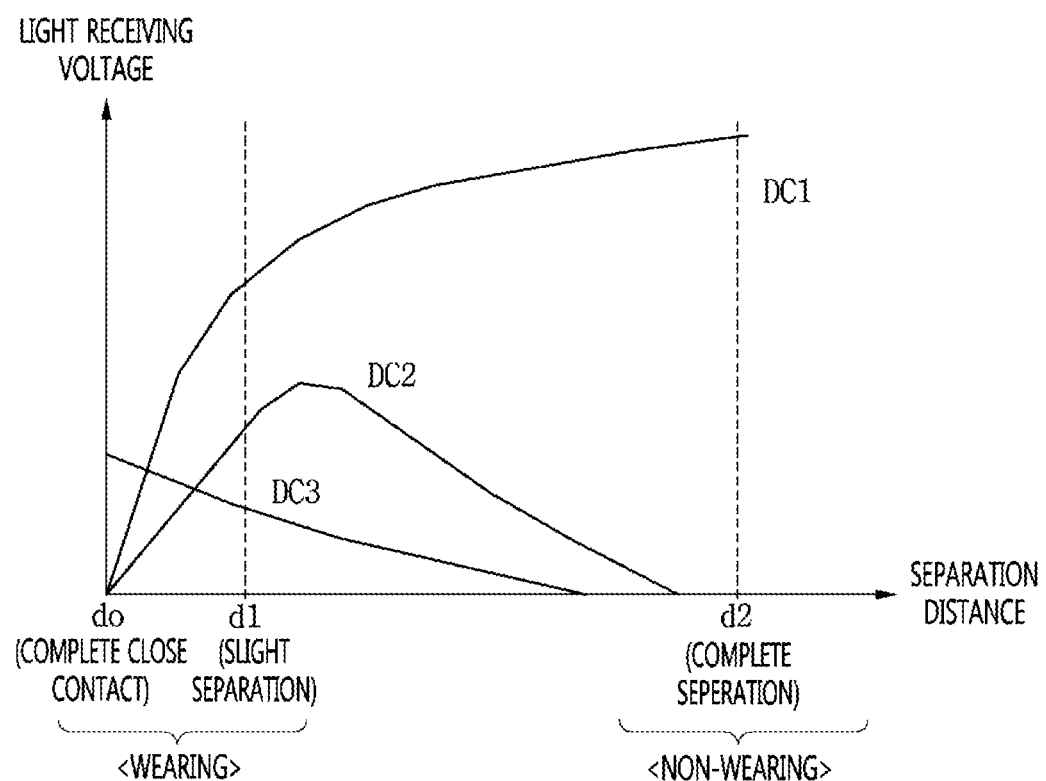
FIG. 5 is a graph illustrating a condition for detecting whether or not to wear a human body wearable device according to an embodiment of the present disclosure.

FIG. 5 is a graph illustrating a condition for detecting whether to wear or not a human body wearable device according to an embodiment of the present disclosure.

Referring to FIG. 5, a light receiving unit 120 receives light from outside, and the light includes first light DC1, second light DC2, and third light DC3, as described above.

The first light DC1 refers to light incident on the light receiving unit 120 by ambient light, as described above.

As shown in FIG. 5, an intensity of the first light DC1 has a minimum value zero in a state in which the human body wearable device 100 is in complete contact with the test object, that is, the separation distance is zero. In addition, the intensity of the first light DC1 increases as the separation distance increases.

Further, the second light DC2 refers to light which is reflected by a surface of the test object and is incident on the light receiving unit 120, as described above.

As shown in FIG. 5, an intensity of the second light DC2 has a maximum value in a state in which the human body wearable device 100 and the test object are spaced apart by a specific gap, and the intensity of the second light DC2 decreases as the separation distance decreases or increases in a specific gap.

Furthermore, the third light DC3 refers to light which is reflected by a skin tissue of the test object and is incident on the light receiving unit 120, as described above.

As shown in FIG. 5, an intensity of the third light DC3 has a maximum value in a state in which the human body wearable device 100 is completely in close contact with the test object, and the intensity of the third light DC3 decreases as the separation distance increases. Then, the intensity of the third light DC3 has a value zero from a moment when the separation distance exceeds a certain distance.

Accordingly, in a state in which the human body wearable device 100 is worn (completely in close contact or spaced apart by a predetermined distance), an intensity of light detected by the light receiving unit 120 varies depending on ON and OFF operations of the light emitting unit 110, but in a state in which the human body wearable device 100 is not worn, an intensity of light detected by the light receiving unit 120 does not vary on the assumption that there is no internal light leakage or external reflection other than a test object.

FIGS. 6 to 8 are diagrams illustrating conditions of a light emitting unit 110 and a light receiving unit 120 according to an embodiment of the present disclosure.

When the control unit 130 enters a wearing detection mode, the light emitting unit 110 outputs a pulse signal for sequentially performing ON and OFF operations.

The light emitting unit 110 sequentially performs the ON and OFF operations according to the pulse signal.

In addition, the control unit 130 detects an intensity of light received through the light receiving unit 120 depending on an operation of the light emitting unit 110 performing the sequential ON and OFF operations.

FIG. 6 illustrates a state of the light emitting unit 110 and the light receiving unit 120 in a state in which the human body wearable device 100 is completely in close contact with a test object. Here, the test object actually refers to a human body.

That is, FIG. 6 illustrates a state of the light emitting unit 110 and the light receiving unit 120 in a state in which the human body wearable device 100 is completely in close contact with a human body.

FIG. 6 (a) illustrates a state of a light emitting unit 110 and a light receiving unit 120 in the condition where ambient light is present, that is, during daytime or in a bright place.

FIG. 6 (b) illustrates a state of a light emitting unit 110 and a light receiving unit 120 in the condition where ambient light is not present, that is, during night time or in a dark place.

Meanwhile, in the following description, a light emitting voltage refers to an intensity of light generated by the light emitting operation of the light emitting unit 110, and a light receiving voltage refers to an intensity of light incident on the light receiving unit 120.

Referring to (a) of FIG. 6, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are completely in close contact with each other, that is, when a separation distance between the human body wearable device 100 and the test object is zero, the ambient light or light reflected on a surface of the test object is not incident on the light receiving unit 120.

Accordingly, only the third light DC3 reflected from a skin tissue of the test object is incident on the light receiving unit 120 in the ON section of the light emitting unit 110, and a light receiving voltage corresponding to the incident third light DC3 is detected.

In addition, in the OFF section of the light emitting unit 110, the light emitting unit 110 does not perform a light emitting operation, so that the third light DC3 is not incident on the light receiving unit 120, and thus a value is zero.

In other words, in a state in which the human body wearable device 100 is completely in close contact with a test object during daytime or a bright place where ambient light is present, the light receiving unit 120 receives third light having a specific light receiving voltage, and all of first to third lights are not received in the OFF section of the light emitting unit 110.

Accordingly, a difference is generated by the intensity of the third light in an intensity of light received through the light receiving unit 120 in the ON section of the light emitting unit 110 and an intensity of light received through the light receiving unit 120 in the OFF section of the light emitting unit 110.

Referring to (b) of FIG. 6, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are completely in close contact with each other, that is, when a separation distance between the human body wearable device 100 and the test object is zero, the ambient light or light reflected on a surface of the test object is not incident on the light receiving unit 120.

Accordingly, only the third light DC3 reflected from a skin tissue of the test object is incident on the light receiving unit 120 in the ON section of the light emitting unit 110, and a light receiving voltage corresponding to the incident third light DC3 is detected.

In addition, in the OFF section of the light emitting unit 110, the light emitting unit 110 does not perform a light emitting operation, so that the third light DC3 is not incident on the light receiving unit 120, and thus a value is zero.

Accordingly, even in a dark place, a difference is generated by the intensity of the third light in an intensity of light received through the light receiving unit 120 in the ON section of the light emitting unit 110 and an intensity of the light received through the light receiving unit 120 in the OFF section of the light emitting unit 110.

FIG. 7 illustrates a state of a light emitting unit 110 and a light receiving unit 120 in a state in which a human body wearable device 100 is slightly separated from a human body (separated by a first distance).

That is, FIG. 7 illustrates a state of the light emitting unit 110 and the light receiving unit 120 in a condition where the human body wearable device 100 is worn on a human body but is not completely in close contact with the human body and is worn so as to be spaced apart by the first distance.

FIG. 7 (*a*) illustrates a state of a light emitting unit 110 and a light receiving unit 120 in the condition where ambient light is present, that is, during daytime or in a bright place. FIG. 7 (*b*) illustrates a state of a light emitting unit 110 and a light receiving unit 120 in the condition where ambient light is not present, that is, during night time or in a dark place.

Referring to (a) of FIG. 7, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated from each other by the first distance, the ambient light, the light reflected from a surface of the test object, and the light reflected from the skin tissue are all incident on the light receiving unit 120.

Accordingly, in the ON section of the light emitting unit 110, the first light DC1 by the ambient light, the second light DC2 corresponding to light reflected from the skin surface, and the third light DC3 reflected from the skin tissue of the test object are all incident on the light receiving unit 120, and thus the light receiving voltages corresponding to the incident first light DC1, second light DC2 and third light DC3 are detected.

In addition, in the OFF section of the light emitting unit 110, the light emitting unit 110 does not perform a light emitting operation, and thus the second light DC2 and the third light DC3 are not incident on the light receiving unit 120.

Accordingly, in the OFF section of the light emitting unit 110, only the first light DC1 is incident on the light receiving unit 120 by the ambient light, and the light receiving voltage corresponding to the first light DC1 is detected.

In other words, in a state in which the human body wearable device 100 is separated from the test object by the first distance during daytime or in a bright place where ambient light is present, the light receiving unit 120 receives all of the first light to the third light in the ON section of the light emitting unit 110 and receives only the first light in the OFF section of the light emitting unit 110.

Accordingly, a difference are generated by the intensity sum of the second and third lights in an intensity of light received through the light receiving unit 120 in the ON section of the light emitting unit 110 and an intensity of light received through the light receiving unit 120 in the OFF section of the light emitting unit 110.

Referring to (b) of FIG. 7, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated from each other by the first distance, the light reflected from a surface of the test object, and the light reflected from the skin tissue are all incident on the light receiving unit 120. That is, since the above condition is a condition in which ambient light is not present, the first light corresponding to the ambient light is not incident on the light receiving unit 120, and thus only the second light and the third light are incident on the light receiving unit 120.

Accordingly, in the ON section of the light emitting unit 110, the second light DC2 corresponding to light reflected from the skin surface, and the third light DC3 reflected from the skin tissue of the test object are incident on the light receiving unit 120, and the light receiving voltages corresponding to the incident second light DC2 and third light DC3 are detected.

In addition, in the OFF section of the light emitting unit 110, the light emitting unit 110 does not perform a light emitting operation, and thus the second light DC2 and the third light DC3 are not incident on the light receiving unit 120, either.

Accordingly, in the OFF section of the light emitting unit 110, the light receiving unit 120 does not receive any of the first to third lights, and thus the light receiving voltage having a value zero is detected.

In other words, in a state in which the human body wearable device 100 is separated from the test object by the first distance during night time or in a dark place where ambient light is not present, the light receiving unit 120 receives the second and third lights in the ON section of the light emitting unit 110, and the first to third lights are not all received in the OFF section of the light emitting unit 110.

Accordingly, even in dark surroundings, a difference are generated by the sum of intensities of the second and third lights in an intensity of light received through the light receiving unit 120 in the ON section of the light emitting unit 110 and an intensity of light received through the light receiving unit 120 in the OFF section of the light emitting unit 110.

FIG. 8 illustrates a state of a light emitting unit 110 and a light receiving unit 120 in a state in which a human body wearable device 100 is completely separated from a human body (separated by a second distance greater than the first distance).

That is, FIG. 8 illustrates a state of the light emitting unit 110 and the light receiving unit 120 in a state in which the human body wearable device 100 is not worn on a human body.

FIG. 8 (a) illustrates a state of a light emitting unit 110 and a light receiving unit 120 in the condition where ambient light is present, that is, during daytime or in a bright place. FIG. 8 (b) illustrates a state of a light emitting unit 110 and a light receiving unit 120 in the condition where ambient light is not present, that is, during night time or in a dark place.

Referring to (a) of FIG. 8, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated by a second distance, light generated through the light emitting unit 110 is not reflected by a surface of the human skin or the skin tissue.

Accordingly, only ambient light is incident on the light receiving unit 120 in the state in which the human body wearable device 100 and the test object are separated by the second distance.

Accordingly, only the first light DC1 due to the ambient light is incident on the light receiving unit 120 in the ON section of the light emitting unit 110, and thus the light receiving voltage corresponding to the incident first light DC1 is detected.

In addition, in the OFF section of the light emitting unit 110, the light emitting unit 110 does not perform a light emitting operation, and thus only the first light DC1 due to the ambient light is incident on the light receiving unit 120.

Accordingly, in the OFF section of the light emitting unit 110, only the first light DC1 is incident on the light receiving unit 120 by the ambient light, and the light receiving voltage corresponding to the first light DC1 is detected.

In other words, in a state in which the human body wearable device 100 is separated from the test object by the second distance during daytime or in a bright place where ambient light is present, the light receiving unit 120 receives only the first light in both the ON and OFF sections of the light emitting unit 110.

Accordingly, the intensity values are the same in an intensity of light received through the light receiving unit 120 in the ON section of the light emitting unit 110 and an intensity of light received through the light receiving unit 120 in the OFF section of the light emitting unit 110.

Referring to (b) of FIG. 8, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated by the second distance, light generated through the light emitting unit 110 is not reflected by the human skin surface or skin tissue. In addition, (b) of FIG. 8 is a condition in which ambient light is not present, and thus in the state in which the human body wearable device 100 and the test object are separated by the second distance, any light is not incident on the light receiving unit 120.

Accordingly, in the ON and OFF sections of the light emitting unit 110, light is not incident on the light receiving unit 120, and a light receiving voltage having a value zero corresponding thereto is detected.

Accordingly, under the condition, the intensity of light has the same value of zero in an intensity of light received through the light receiving unit 120 in the ON section of the light emitting unit 110 and an intensity of light received through the light receiving unit 120 in the OFF section of the light emitting unit 110.

As shown in FIGS. 6 and 7, in a state in which the human body wearable device 100 is worn on a human body, a light receiving voltage of the light receiving unit 120 in the ON section of the light emitting unit 110 and a light receiving voltage of the light receiving unit 120 in the OFF section of the light emitting unit 110 are not the same and have different values of a certain magnitude.

Further, as shown in FIG. 8, in a state in which the human body wearable device 100 is not worn on a human body, light receiving voltages of light incident on the light receiving unit 120 in the ON and OFF sections of the light emitting unit 110 are the same.

Accordingly, the control unit 130 determines a state whether the human body wearable device 100 is worn on a human body or not based on a difference value depending on an intensity of each light incident through the light receiving unit 120 in the ON and OFF sections of the light emitting unit 110.

That is, the control unit 130 determines a wearing state of the human body wearable device 100 according to the following equation.

$$V\,ON - V\,OFF = 0, \text{ a non-wearing state}$$

$$V\,ON - V\,OFF > 0, \text{ a wearing state} \qquad \text{[Equation 1]}$$

Here, V ON represents an intensity of light incident on the light receiving unit 120 in the ON section of the light emitting unit 110, and V OFF represents an intensity of light incident on the light receiving unit 120 in the OFF section of the light emitting unit 110.

Meanwhile, the equation 1 is an equation in an ideal condition.

However, in a state in which the human body wearable device 100 is not actually worn, direct light leakage from the light emitting element to a light receiving element may occur depending on a mechanism condition, and light reflection by an external environment may be present.

Accordingly, even in a state in which the human body wearable device 100 is not worn, the difference value between V ON and V OFF may be a specific value other than zero.

Accordingly, in an embodiment, in a state in which the human body wearable device 100 is not worn, a difference between V ON and V OFF is measured (that is, an amount of direct light leakage from a light emitting element to a light receiving element and an amount of light reflection due to an external environment), and thus the following equation 2 for detecting an accurate wearing state of the human body wearable device 100 is determined.

$$V\,ON - V\,OFF \leq V\,TH, \text{ a non-wearing state}$$

$$V\,ON - V\,OFF > V\,TH, \text{ a wearing state} \qquad \text{[Equation 2]}$$

Here, V ON represents an intensity of light incident on the light receiving unit 120 in the ON section of the light emitting unit 110, and V OFF represents an intensity of light incident on the light receiving unit 120 in the OFF section of the light emitting unit 110, and V TH is a threshold voltage for determining an wearing state of the human body wearable device 100.

Accordingly, although the control unit 130 may detect a wearing state of the human body wearable device 100 via the equation 1, in order to detect the wearing state more accurately, a threshold voltage is determined based on an amount of light leakage and an amount of light reflection, and when an intensity of the light incident on the light receiving unit 120 in the ON section of the light emitting unit 110 and an intensity of the light incident on the light receiving unit 120 in the OFF section of the light emitting unit 110 are greater than the threshold value, the human body wearable device 100 is determined to be worn on the human body.

Figure 9:
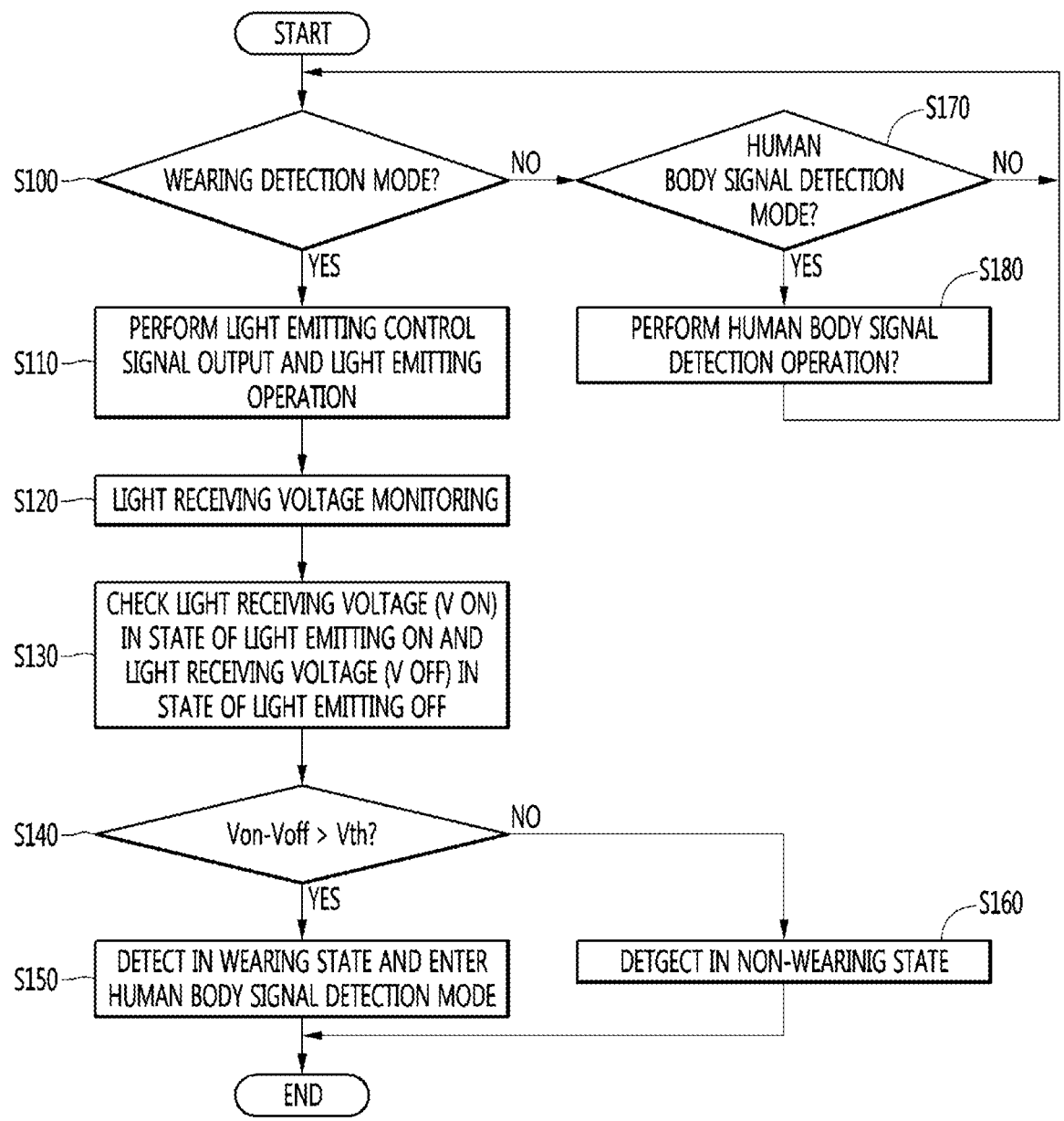
FIG. 9 is a flowchart for explaining a step by step operation method of a human body wearable device according to a first embodiment of the present disclosure.

FIG. 9 is a flowchart for explaining a step by step operation method of a human body wearable device 100 according to a first embodiment of the present disclosure.

Referring to FIG. 9, the control unit 130 determines whether the human body wearable device 100 is in a wearing detection mode, or a human body signal detection mode in step S100.

As a result of the determination in step S100, if the mode of the human body wearable device 100 is the wearing detection mode, the control unit 130 outputs a light emitting control signal for controlling an operation of the light emitting unit 110, and the light emitting unit 110 performs a light emitting operation (sequentially performing ON and OFF operations) depending on the light emitting control signal in step S110.

The control unit 130 monitors an intensity of the light incident on the light receiving unit 120 depending on an light emitting operation of the light emitting unit 110 in step S120.

Then, the control unit 130 checks a first light receiving voltage V ON with respect to an intensity of light incident on the light receiving unit 120 in the ON section of the light emitting unit 110 and a second light receiving voltage V OFF with respect to an intensity of light incident on the light receiving unit 120 in the OFF section of the light emitting unit 110.

In addition, the control unit 130 detects a difference value between the first light receiving voltage and the second light receiving voltage and determines whether the difference value is greater than a predetermined threshold value in step S140.

Then, if the above difference value is greater than the predetermined threshold value, the control unit 130 detects a wearing state of the human body wearable device 100, and thus, the control unit 130 may enter the human body signal detection mode in step S150.

Further, if the above difference value is not greater than the predetermined threshold value (if less than or equal to), the control unit 130 detects the human body wearable device 100 in a state in which the human body wearable device 100 is not worn in step S160.

Meanwhile, as a result of the determination in step S100, if the mode of the human body wearable device 100 is not the wearing detection mode, the control unit 130 determines whether the human body wearable device 100 is in the human body signal detection mode in step S170, and if the mode of the human body wearable device 100 is the human body signal detection mode, the control unit 130 performs the human body signal detection operation in step S180.

Meanwhile, although the human body wearable device 100 may be detected to be in a state in which the human body wearable device 100 is worn on a test object by the above method, whether the test object is a human body or a thing may not be accurately detected.

Figure 10:
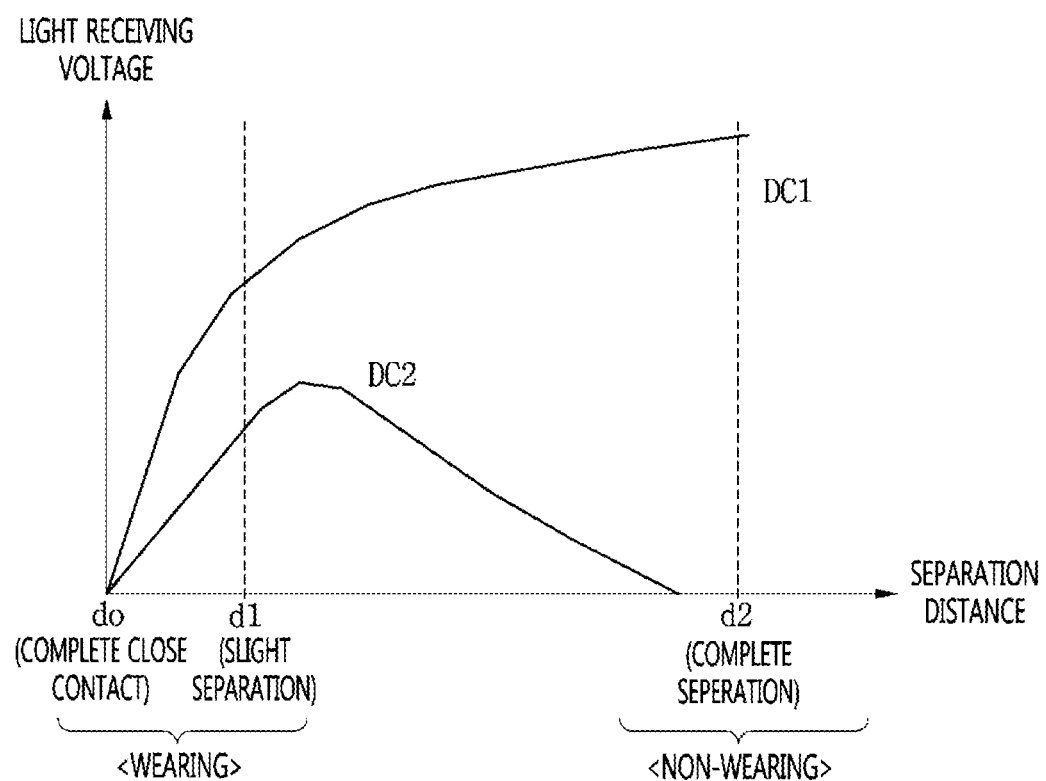
FIG. 10 is a graph illustrating changes in a light receiving voltage with respect to light incident on a light receiving unit in a state in which a human body wearable device according to an embodiment is in contact with a thing.

FIG. 10 is a graph illustrating changes in the light receiving voltage with respect to light incident on a light receiving unit in a state in which a human body wearable device 100 is in contact with a thing.

When the human body wearable device 100 contacts a thing, light corresponding to the first light DC1 and the second light DC2 is incident on the light receiving unit 120. That is, since the thing does not have a skin tissue, the third light DC3 representing light reflected from the skin tissue is not incident on the light receiving unit 120.

As shown in FIG. 10, an intensity of the first light DC1 has a minimum value zero in a state in which the human body wearable device 100 is in complete contact with the test object, that is, a separation distance is zero. In addition, an intensity of the first light DC1 increases as the separation distance increases.

Further, the second light DC2 refers to light which is reflected by a surface of the test object and is incident on the light receiving unit 120, as described above.

As shown in FIG. 10, an intensity of the second light DC2 has a maximum value in a state in which the human body wearable device 100 and the test object are spaced apart by a specific gap, and the intensity of the second light DC2 decreases as the separation distance decreases or increases in the specific gap.

FIGS. 11 to 13 are diagrams illustrating states of a light emitting unit 110 and a light receiving unit 120 depending on conditions when the human body wearable device 100 is not in contact with a human body but in contact with a thing.

That is, FIG. 11 illustrates a state of the light emitting unit 110 and the light receiving unit 120 in a state in which the human body wearable device 100 is completely in close contact with a thing.

FIG. 11 (a) illustrates a state of a light emitting unit 110 and a light receiving unit 120 in the condition where ambient light is present, that is, during daytime or in a bright place. FIG. 11 (b) illustrates a state of a light emitting unit 110 and a light receiving unit 120 in the condition where ambient light is not present, that is, during night time or in a dark place.

Here, in a state in which the human body wearable device 100 is completely in close contact with a thing, that is, when a separation distance between the human body wearable device 100 and the test object is zero, the ambient light or light reflected from a surface of the test object is not incident on the light receiving unit 120.

Accordingly, specific light is not incident on the light receiving unit 120 in the ON section of the light emitting unit 110.

In addition, in the OFF section of the light emitting unit 110, the light emitting unit 110 does not perform a light emitting operation, and thus light is not incident on the light receiving unit 120.

In other words, in a state in which the human body wearable device 100 is completely in close contact with the test object during daytime or in a bright place where ambient light is present, the light receiving unit 120 does not receive light in the ON and OFF sections of the light emitting unit 110.

Accordingly, the intensity values of both lights are the same in an intensity of light received through the light receiving unit 120 in the ON section of the light emitting unit 110 and an intensity of light received through the light receiving unit 120 in the OFF section of the light emitting unit 110.

In (b) of FIG. 11 similar to (a) of FIG. 6, accordingly, light is not incident on the light receiving unit 120 in the ON and OFF sections of the light emitting unit 110.

Accordingly, even in a dark place, the intensity values of both lights are the same in an intensity of light received through the light receiving unit 120 in the ON section of the light emitting unit 110 and an intensity of light received through the light receiving unit 120 in the OFF section of the light emitting unit 110.

Meanwhile, the conditions are the same as the conditions in (a) and (b) of FIG. 8, values of light receiving voltages in the ON and OFF sections are the same, and thus it is possible to accurately detect the state in which the human body wearable device 100 is not worn on a human body in a state in which the human body wearable device 100 is completely in close contact with a thing as described above.

FIG. 12 illustrates a state of a light emitting unit 110 and a light receiving unit 120 in a state in which a human body wearable device 100 is slightly separated from a thing (separated by a first distance).

That is, FIG. 12 illustrates a state of the light emitting unit 110 and the light receiving unit 120 when the human body wearable device 100 is placed in a position separated by the first distance from a thing.

FIG. 12 (*a*) illustrates a state of a light emitting unit 110 and a light receiving unit 120 in the condition where ambient light is present, that is, during daytime or in a bright place. FIG. 12 (*b*) illustrates a state of a light emitting unit 110 and a light receiving unit 120 in the condition where ambient light is not present, that is, during night time or in a dark place.

Referring to (a) of FIG. 12, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated from each other by the first distance, ambient light and light reflected from a surface of the test object are all incident on the light receiving unit 120.

Accordingly, in the ON section of the light emitting unit 110, the first light DC1 by the ambient light and the second light DC2 corresponding to light reflected from the skin surface are all incident on the light receiving unit 120, and thus the light receiving voltages corresponding to the incident first light DC1, and second light DC2 are detected.

In addition, in the OFF section of the light emitting unit 110, the light emitting unit 110 does not perform a light emitting operation, and thus the second light DC2 is not incident on the light receiving unit 120.

Accordingly, in the OFF section of the light emitting unit 110, only the first light DC1 is incident on the light receiving unit 120 by the ambient light, and the light receiving voltage corresponding to the first light DC1 is detected.

In other words, in a state in which the human body wearable device 100 is separated from the test object (a thing) by the first distance during daytime or in a bright place where ambient light is present, the light receiving unit 120 receives the first light to the second light in the ON section of the light emitting unit 110 and receives only the first light in the OFF section of the light emitting unit 110.

Accordingly, a difference is generated by the intensity of the second light in an intensity of light received through the light receiving unit 120 in the ON section of the light emitting unit 110 and an intensity of light received through the light receiving unit 120 in the OFF section of the light emitting unit 110.

Referring to (b) of FIG. 12, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object (a thing) are separated from each other by the first distance, only light reflected from a surface of the test object is incident on the light receiving unit 120. That is, since the above condition is a condition in which ambient light is not present, the first light corresponding to the ambient light is not incident on the light receiving unit 120, and thus only the second light is incident on the light receiving unit 120.

Accordingly, in the ON section of the light emitting unit 110, the light receiving unit 120 detects a light receiving voltage corresponding to the second light DC2 according to light reflected from a surface of the test object.

In addition, in the OFF section of the light emitting unit 110, the light emitting unit 110 does not perform a light emitting operation, and thus the second light DC2 is not incident on the light receiving unit 120, either.

Accordingly, in the OFF section of the light emitting unit 110, the light receiving unit 120 does not receive any of the first and second lights, and thus the light receiving voltage having a value zero is detected.

In other words, in a state in which the human body wearable device 100 is separated from the test object by the first distance during night time or in a dark place where ambient light is not present, the light receiving unit 120 receives the second light in the ON section of the light emitting unit 110, and both of the first and second lights are not received in the OFF section of the light emitting unit 110.

Accordingly, even in a dark surrounding environment, a difference is generated by the intensity of the second light in an intensity of light received through the light receiving unit 120 in the ON section of the light emitting unit 110 and an intensity of light received through the light receiving unit 120 in the OFF section of the light emitting unit 110.

Accordingly, in a state in which the human body wearable device 100 is separated from a thing by the first distance, a difference by an intensity of second light occurs between a light receiving voltage in the ON section and a light receiving voltage in the OFF section, and thus, even with the equation 1 or 2, the human body wearable device 100 may not accurately detect a state whether the human body wearable device 100 is worn on a human body, not a thing.

FIG. 13 illustrates a state of a light emitting unit 110 and a light receiving unit 120 in a state in which a human body wearable device 100 is completely separated from a thing (separated by a second distance greater than the first distance).

That is, FIG. 13 illustrates a state of the light emitting unit 110 and the light receiving unit 120 in a state in which the human body wearable device 100 is not in contact with a thing.

FIG. 13 (*a*) illustrates a state of a light emitting unit 110 and a light receiving unit 120 in the condition where ambient light is present, that is, during daytime or in a bright place. FIG. 13 (*b*) illustrates a state of a light emitting unit 110 and a light receiving unit 120 in the condition where ambient light is not present, that is, during night time or in a dark place.

Referring to (a) of FIG. 13, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated by the second distance, light generated through the light emitting unit 110 is not reflected by a surface of the thing.

Accordingly, only ambient light is incident on the light receiving unit 120 in a state in which the human body wearable device 100 and the test object are separated by the second distance.

Accordingly, only the first light DC1 is incident on the light receiving unit 120 in the ON section of the light emitting unit 110 due to the ambient light, and thus the light receiving voltage corresponding to the incident first light DC1 is detected.

In addition, in the OFF section of the light emitting unit 110, the light emitting unit 110 does not perform a light emitting operation, and thus only the first light DC1 due to the ambient light is incident on the light receiving unit 120.

Accordingly, in the OFF section of the light emitting unit 110, only the first light DC1 is incident on the light receiving unit 120 by the ambient light, and the light receiving voltage corresponding to the first light DC1 is detected.

In other words, in a state in which the human body wearable device 100 is separated from the test object by the second distance during daytime or in a bright place where ambient light is present, the light receiving unit 120 receives only the first light in both of the ON and OFF sections of the light emitting unit 110.

Accordingly, the intensity values are the same in an intensity of light received through the light receiving unit 120 in the ON section of the light emitting unit 110 and an intensity of light received through the light receiving unit 120 in the OFF section of the light emitting unit 110.

Referring to (b) of FIG. 13, the light emitting unit 110 generates light having a specific light emitting voltage in a ON section depending on a pulse signal of the control unit 130, and does not generate light in a OFF section.

At this point, the light receiving unit 120 receives the light in the ON and OFF sections of the light emitting unit 110, respectively.

Here, in a state in which the human body wearable device 100 and the test object are separated by the second distance, light generated through the light emitting unit 110 is not reflected by a surface of the thing. In addition, (b) of FIG. 13 is a condition in which ambient light is not present, and thus in a state in which the human body wearable device 100 and the test object are separated by the second distance, any light is not incident on the light receiving unit 120.

Accordingly, in the ON and OFF sections of the light emitting unit 110, light is not incident on the light receiving unit 120, and a light receiving voltage having a value zero corresponding thereto is detected.

Accordingly, under the condition, the intensity of light has the same value of zero in an intensity of light received through the light receiving unit 120 in the ON section of the light emitting unit 110 and an intensity of light received through the light receiving unit 120 in the OFF section of the light emitting unit 110.

As described above, when the human body wearable device 100 is separated from the thing by the first distance, a difference between the first light receiving voltage in the ON section and the second light receiving voltage in the OFF section occurs, and thus only the difference between the first light receiving voltage and the second light receiving voltage may not accurately detect whether the human body wearable device 100 is worn on a human body or not.

Therefore, in an embodiment, when the state of the human body wearable device 100 is detected to be in a wearing state, the human body wearable device 100 performs a further determination process to detect whether the object is a human body or a thing.

For this, the control unit 130 detects a signal depending on operations of the light emitting unit 110 and the light receiving unit 120 and analyzes the detected signal to determine whether the object is a human body or a thing.

Figure 14:
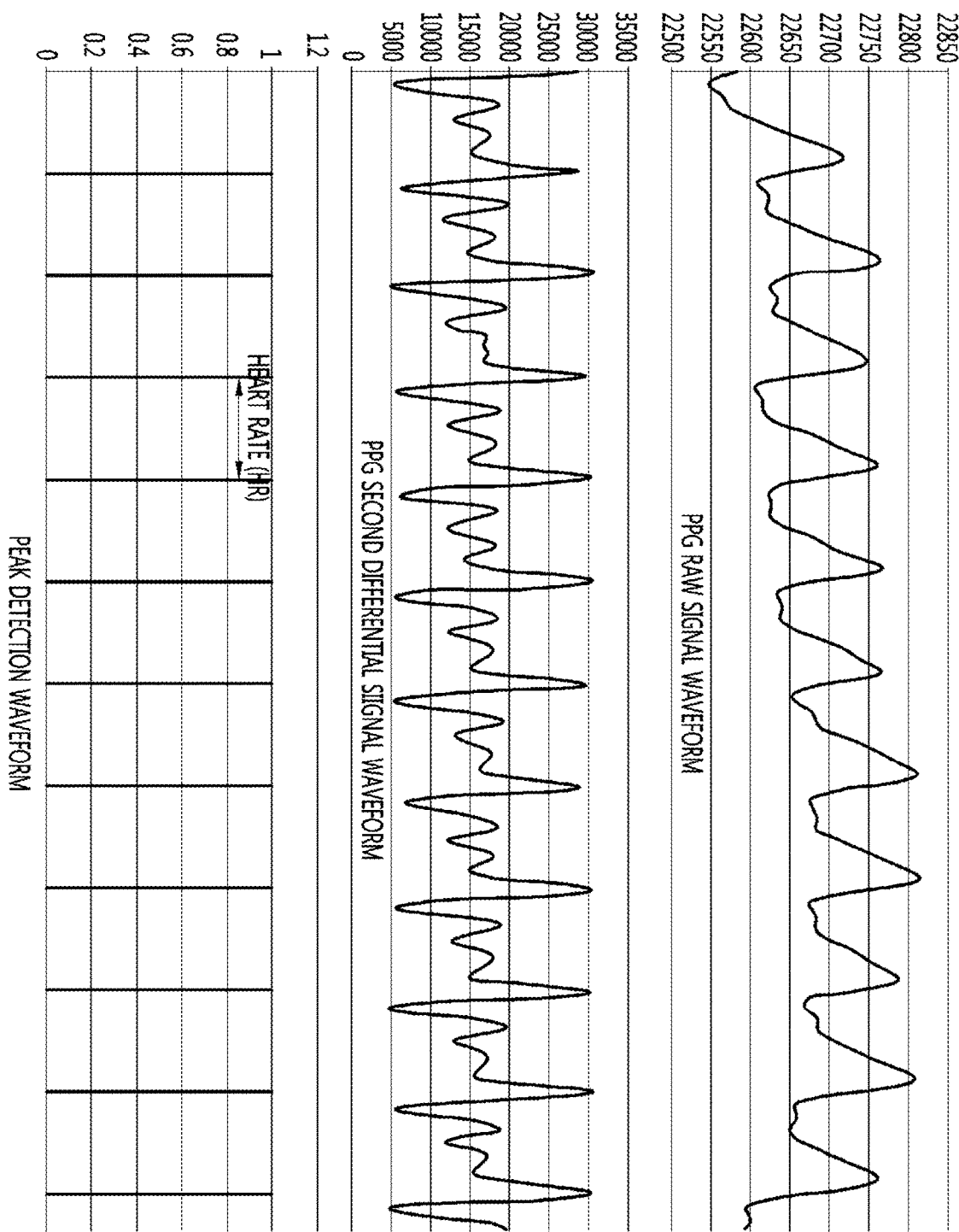
FIG. 14 is a diagram illustrating signals detected according to an embodiment of the present disclosure.

FIG. 14 is a diagram illustrating signals detected according to an embodiment of the present disclosure.

As shown in FIG. 14, the control unit 130 detects a photoplethysmography (PPG) raw signal waveform connecting only the light receiving voltage in the ON section among the light receiving voltages received through the light receiving unit 120.

In addition, the control unit 130 detects a second-order differential signal waveform obtained by secondarily differentiating the PPG raw signal waveform.

Then, the control unit 130 extracts only peak signals included in the second-order differential signal waveform to detect a peak waveform, and detects a heart rate (HR) among the peak signals within the detected peak waveform.

At this point, in the case of the state in which the human body wearable device 100 is worn on a human body, the HR is in a range of 30 to 240 bpm (beat per minute), and thus the control unit 130 determines whether the HR is within the range of 30 to 240 bpm.

In addition, if the heart rate (HR) is within the range of 30 to 240 bpm, the control unit 130 determines the human body wearable device 100 which is worn on a human body, and if the heart rate (HR) exceeds the range of 30 to 240 bpm, the control unit 130 determines the human body wearable device 100 worn on a thing.

As described above, according to an embodiment of the present disclosure, it is possible to accurately detect whether the human body wearable device is worn on a human body regardless of daytime or a bright place due to lighting, and a night time or a dark place.

In addition, according to an embodiment of the present disclosure, it is possible to precisely distinguish when the human body wearable device is in contact with a thing other than a human body and to prevent various malfunctions that may occur when the human body wearable device is brought into contact with a thing.

Figure 15:
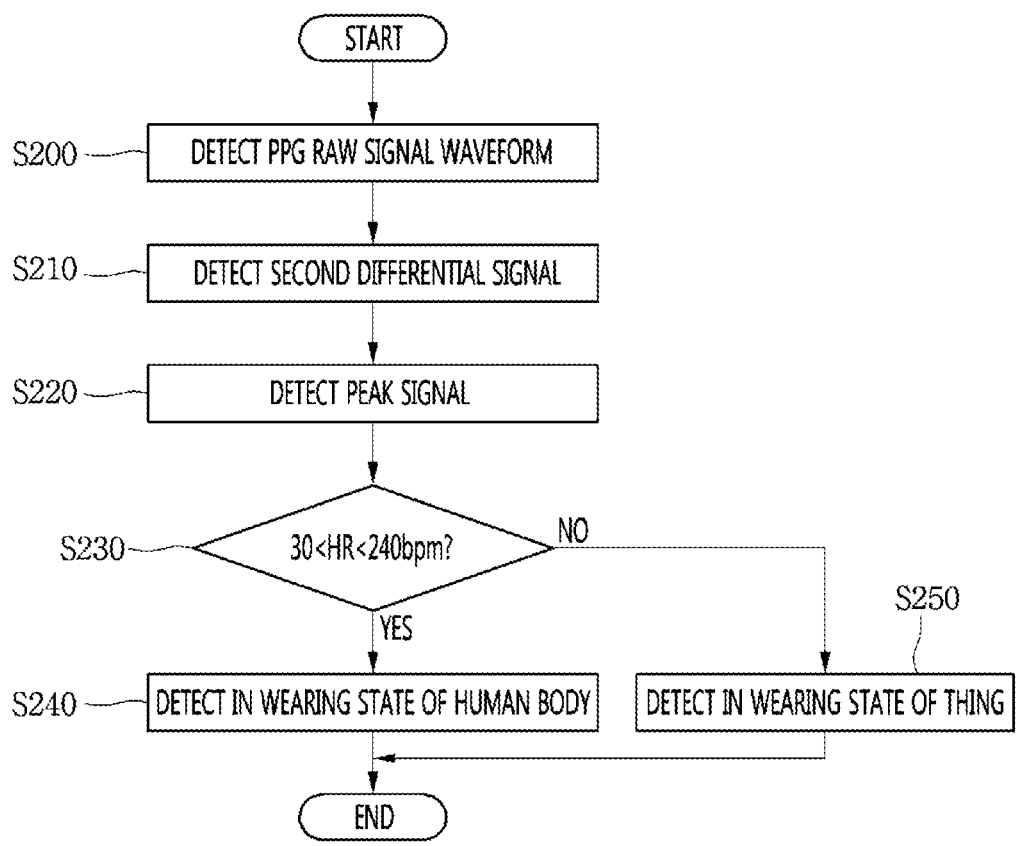
FIG. 15 is a flowchart for describing a step by step method for detecting an object on which a human body wearable device according to an embodiment of the present disclosure is worn.

FIG. 15 is a flowchart for describing a step by step method for detecting an object to be worn by a human body wearable device 100 according to an embodiment of the present disclosure.

Referring to FIG. 15, the control unit 130 detects a PPG raw signal waveform by connecting only a light receiving voltage corresponding to the ON section of the light emitting unit 110 among the light receiving voltages of the light receiving unit 120 in step S200.

Then, the control unit 130 secondarily differentiates the detected PPG raw signal waveform to detect a secondary differential signal in step S210.

In addition, the control unit 130 detects only a peak signal from the detected secondary differential signal in step S220.

Further, the control unit 130 determines whether the heart rate (HR) between the peak signals falls within a range of 30 to 240 bpm based on the detected peak signal in step S230.

Then, when the heart rate (HR) between the peak signals falls within the range of 30 to 240 bpm, the control unit 130 determines that the human body wearable device 100 is currently worn on a human body in step S240, and if the heart rate (HR) exceeds the range of 30 to 240 bpm, the control unit 130 determines that the human body wearable device 100 is currently worn (or in contact with) on a thing in step S250.

As described above, according to an embodiment of the present disclosure, it is possible to accurately detect whether the human body wearable device is worn on a human body regardless of daytime or a bright place due to lighting, and a night time or a dark place.

In addition, according to an embodiment of the present disclosure, it is possible to precisely distinguish when the human body wearable device is in contact with a thing other than a human body and to prevent various malfunctions that may occur when the human body wearable device is brought into contact with a thing.

Figure 16:
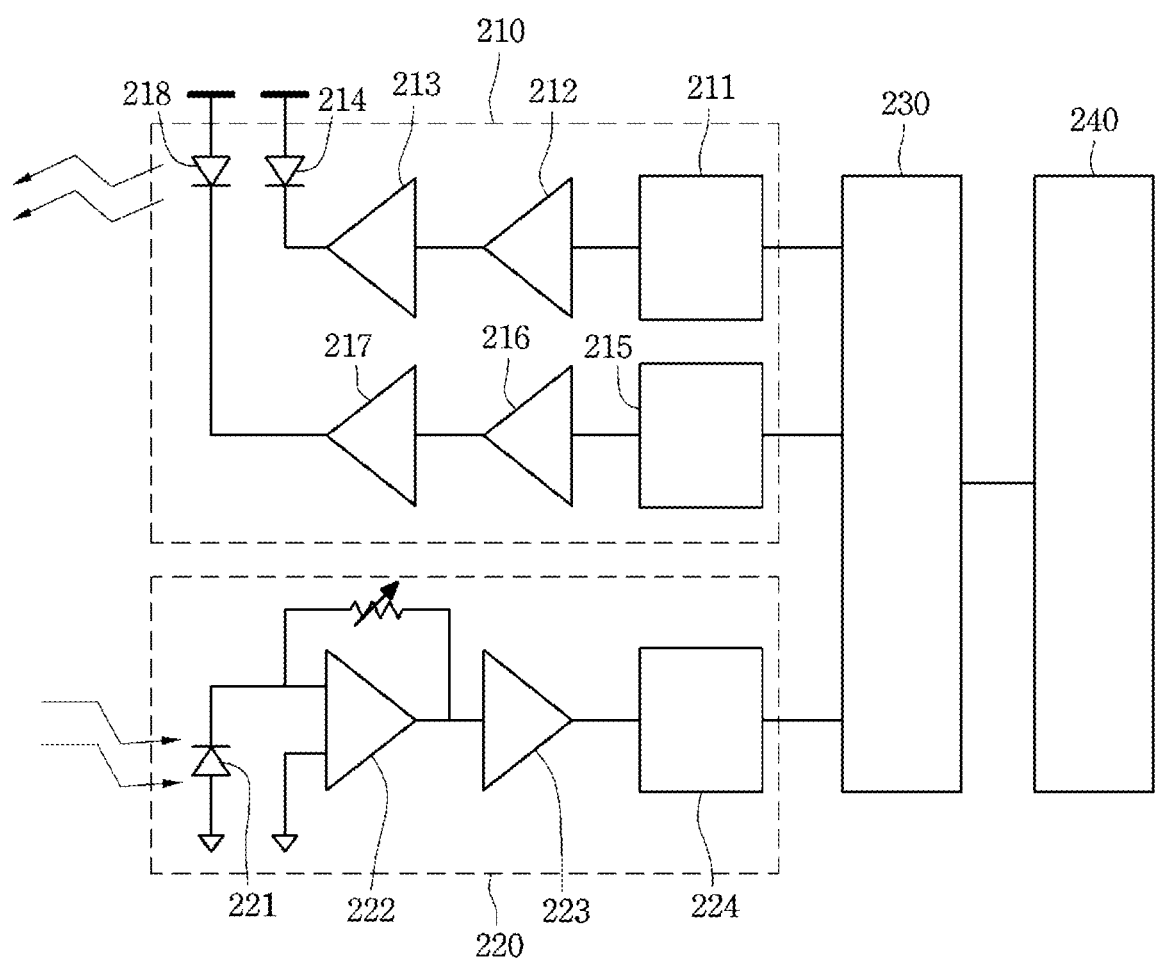
FIG. 16 is a diagram illustrating a configuration of a human body wearable device according to a second embodiment of the present disclosure.

FIG. 16 is a diagram illustrating a configuration of a human body wearable device 200 according to a second embodiment of the present disclosure.

Referring to FIG. 16, the human body wearable device 200 includes a light emitting unit 210, a light receiving unit 220 and a control unit 230.

The light emitting unit 210 includes a first light emitting unit and a second light emitting unit.

The first light emitting unit includes: a first digital-analog converter 211 for converting a digital signal output via the control unit 230 into an analog signal, a first amplifier 212 for primarily amplifying the signal converted via the first digital-analog converter 211, a second amplifier 213 for secondarily amplifying the signal primarily amplified via the first amplifier 212, and a first light emitting element 214 for generating light based on the secondarily amplified signal.

Here, the first digital-analog converter 211 converts the digital signal into an analog signal in order to set a current of a first light emitting element 214.

Further, the first amplifier 212 and the second amplifier 213 are signal amplifying units for supplying an alternating current necessary for driving the first light emitting element 214 to the first light emitting element 214.

Furthermore, the first light emitting element 214 may be implemented with a light emitting diode (LED).

The second light emitting unit includes the same configuration as the first light emitting unit, and preferably includes: a second digital-analog converter 215, a first amplifier 216 for primarily amplifying the signal converted via the second digital-analog converter 215, a second amplifier 217 for secondarily amplifying the signal primarily amplified via the first amplifier 216, and a second light emitting element 218 for generating light based on the secondarily amplified signal.

That is, when the human body wearable device 200 according to the second embodiment is compared with the human body wearable device 100 according to the first embodiment, the light emitting unit is configured with a plurality of light emitting units, which is different.

In other words, the human body wearable device 100 according to the first embodiment includes only one light emitting unit which generates light of a specific wavelength band.

In addition, the human body wearable device 200 according to the second embodiment includes a first light emitting unit for generating light of a first wavelength and a second light emitting unit for generating light of a second wavelength different from the first wavelength.

That is, the first light emitting element 214 constituting the first light emitting unit may be a red light emitting diode which emits light having a wavelength of 660 nm, and the second light emitting element 218 constituting the second light emitting unit may be an infrared light emitting diode which emits light having a wavelength of 940 nm.

In other words, the light corresponding to the infrared wavelength and the red wavelength has different absorption characteristics depending on whether the hemoglobin in the blood contains oxygen or not.

Accordingly, the control unit 230 measures the oxygen saturation of blood based on the light receiving voltage of the light receiving unit 220 according to the operation of the first light emitting unit, and the light receiving voltage of the light receiving unit 220 according to the operation of the second light emitting unit.

At this point, the light emitting operations of the first light emitting unit and the second light emitting unit are performed by a pulse signal output through the control unit 230.

The pulse signal includes a first section for turning ON the second light emitting unit, a second section for turning OFF both the first light emitting unit and the second light emitting unit, a third section for turning ON the first light emitting unit, a fourth section for turning OFF both the first light emitting unit and the second light emitting unit, which are repeated.

Accordingly, the control unit 230 uses one or more of the light receiving voltage corresponding to the operation of the first light emitting unit and the light receiving voltage corresponding to the operation of the second light emitting unit, and thus it is possible to perform an operation of detecting a wearing state as described in the first embodiment.

In addition, the light receiving unit 220 receives incident light including light reflected from a test object depending on a light emitting operation of the light emitting unit 210.

The light receiving unit 220 includes a light receiving element 221 for receiving the incident light, a first amplifier 222 for primarily amplifying an optical signal incident via the light receiving element 221, a second amplifier 223 for secondarily amplifying a signal primarily amplified via the first amplifier 222, and an analog-digital converter 224 for converting a signal secondarily amplified via the second amplifier 223 into a digital signal.

The light receiving element 221 receives light incident from the outside. At this point, the light receiving element 221 may be implemented with a photodiode (PD) or a transistor (TR).

In addition, the first amplifier 222 converts a weak photocurrent detected by the light receiving element 221 into a voltage and amplifies the voltage, which may be a transimpedance amplifier (TIA).

Further, the second amplifier 223 amplifies a voltage amplified via the first amplifier 222 to a voltage of sufficient magnitude to be processed by the analog-digital converter 224.

Furthermore, the analog-digital converter 224 converts an analog voltage to an equivalent digital voltage according to a specified sampling rate.

The control unit 230 controls operations of the light emitting unit 210 and the light receiving unit 220.

For this, a detailed description will be omitted for the parts overlapping with the first embodiment.

First, the control unit 230 operates the light emitting unit of either the first light emitting unit or the second light emitting unit in the case of entering the wearing state detection mode, thereby detecting a wearing state as described in the first embodiment.

In addition, in the case of detecting in a wearing state, the control unit 230 performs an operation of determining whether or not the object on which the human body wearable device 200 is worn is a human body or a thing, and the operation is the same as described in the first embodiment.

At this point, it is preferable that the light emitting unit used for determining a wearing object is assigned to the first light emitting unit for measuring the heart rate (HR).

Further, in the case of determining that the human body wearable device 200 is worn on a human body, the control unit 230 controls operations of the first light emitting unit and the second light emitting unit and periodically detects oxygen saturation of blood.

In addition, the control unit 230 displays state information of a human body including the detected heart rate and oxygen saturation of blood on a display unit 240.

Figure 17:
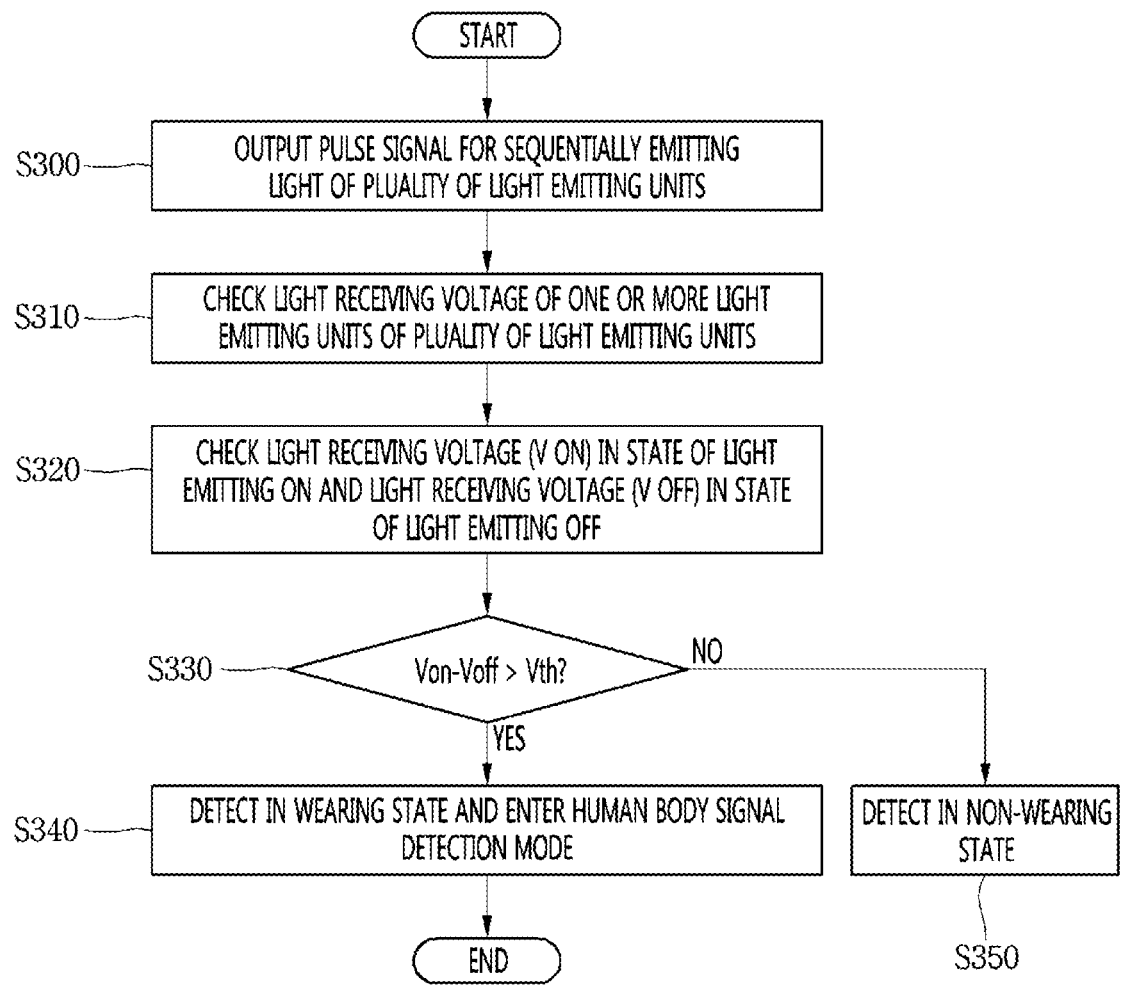
FIG. 17 is a flowchart for explaining a step by step operation method of a human body wearable device according to a second embodiment of the present disclosure.

FIG. 17 is a flowchart for explaining a step by step operation method of a human body wearable device according to a second embodiment of the present disclosure.

Referring to FIG. 17, the control unit 230 outputs a pulse signal for sequentially emitting light of a plurality of light emitting units in step S300.

Then, the control unit 230 checks a light receiving voltage of a light receiving unit corresponding to light generated by one or more light emitting units of the plurality of light emitting units sequentially emitting light by the pulse signal in step S310.

Then, the control unit 230 checks the checked light receiving voltage with a first light receiving voltage in the light in the ON section of the light emitting unit and a second light receiving voltage in the OFF section of the light emitting unit, respectively in step S320.

In addition, the control unit 230 checks a difference between the first light receiving voltage and the second light receiving voltage and determines whether the checked difference value is greater than a predetermined threshold value V TH in step S330.

Then, if the difference value is greater than the predetermined threshold value, the control unit 230 determines the state of the human body wearable device which is in a wearing state, and thus, the control unit 230 enters a human body signal detection mode in step S340.

Further, if the above difference value is not greater than the predetermined threshold value, the control unit 230 determines the state of the human body wearable device which is in a non-wearing state in step S350.

Figure 18:
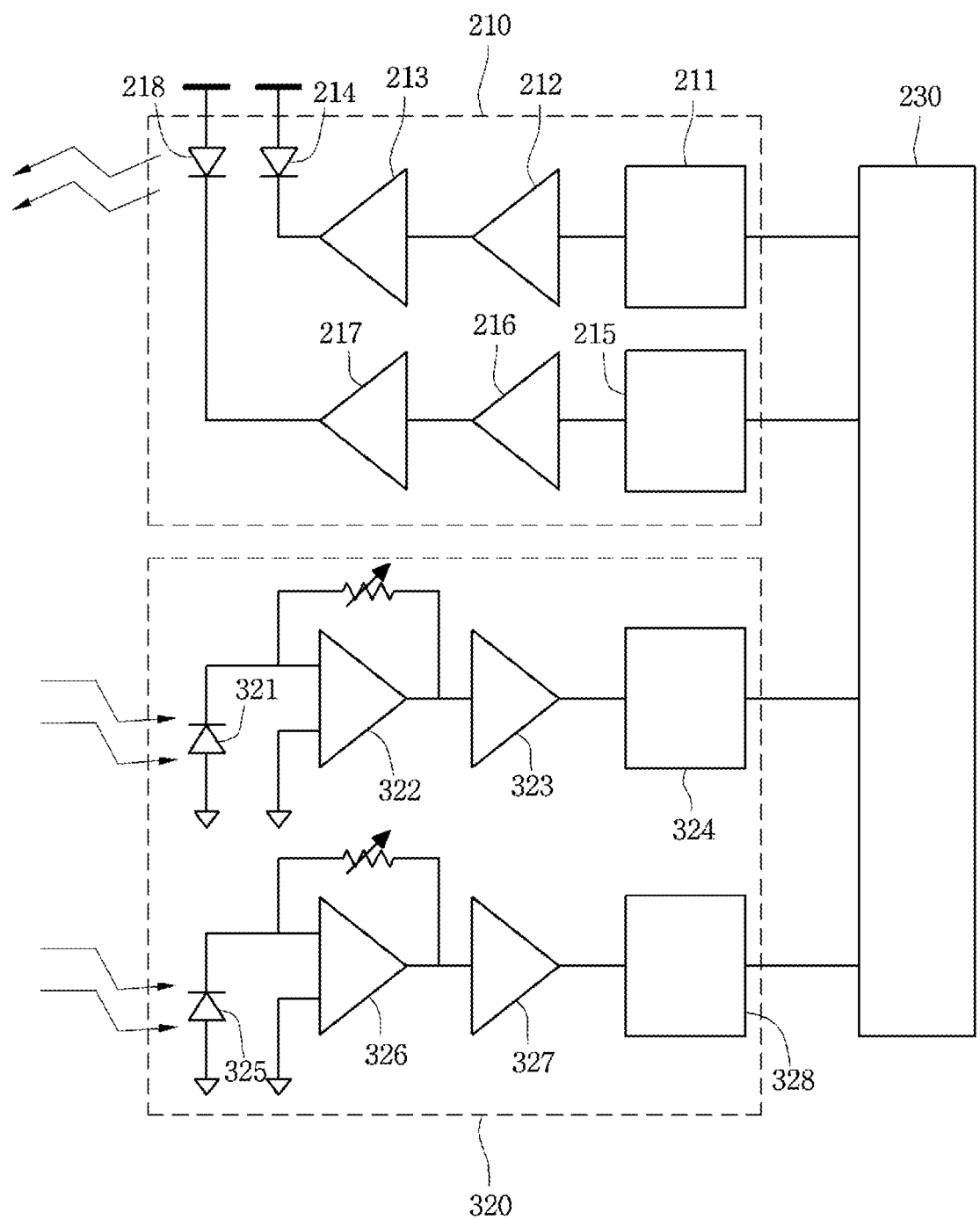
FIG. 18 is a diagram illustrating a configuration of a human body wearable device according to a third embodiment of the present disclosure.

FIG. 18 is a diagram illustrating a configuration of a human body wearable device 300 according to a third embodiment of the present disclosure.

Referring to FIG. 18, the human body wearable device 300 includes a light emitting unit 310, a light receiving unit 320 and a control unit 330.

Here, the human body wearable device 300 is the same as the human body wearable device 100 according to the first embodiment, except that a plurality of light emitting units and a plurality of light receiving units are provided.

That is, the human body wearable device 100 in the first embodiment detects a human body signal in a human body signal detection mode by using one light emitting unit and light receiving unit. In addition, the wearing state is detected in the wearing state detection mode.

However, in the third embodiment, a light emitting unit and a light receiving unit for detecting a human body signal, and a light emitting unit and a light receiving unit for detecting a wearing state are separately formed, respectively.

Accordingly, the human body wearable device 300 according to the third embodiment periodically detects a human body signal and also detects a wearing state.

The first light emitting unit includes a first digital-analog converter 311 for converting a digital signal output via the control unit 330 into an analog signal, a first amplifier 312 for primarily amplifying the signal converted via the first digital-analog converter 311, a second amplifier 313 for secondarily amplifying the signal primarily amplified via the first amplifier 312, and a first light emitting element 314 for generating light based on the secondarily amplified signal.

Here, the first digital-analog converter 311 converts the digital signal into an analog signal in order to set a current of the first light emitting element 314.

Further, the first amplifier 312 and the second amplifier 313 are signal amplifying units for supplying an alternating current necessary for driving the light emitting element 314 to the first light emitting element 314.

Furthermore, the first light emitting element 314 may be implemented with a light emitting diode (LED).

The second light emitting unit includes the same configuration as the first light emitting unit, and preferably includes a second digital-analog converter 315, a first amplifier 316 for primarily amplifying the signal converted via the second digital-analog converter 315, a second amplifier 317 for secondarily amplifying the signal primarily amplified via the first amplifier 316, and a second light emitting element 318 for generating light based on the secondarily amplified signal.

In addition, the first light emitting element 214 and the second light emitting element 218 may generate light of the same wavelength to each other, and can alternatively generate light of a different wavelength.

In addition, the light receiving unit 320 includes a first light receiving unit for receiving light incident depending on an operation of the first light emitting unit, and a second light receiving unit for receiving light incident depending on an operation of the second light emitting unit.

The first light receiving unit includes a first light receiving element 321 for receiving the incident light, a first amplifier 322 for primarily amplifying an optical signal incident via the first light receiving element 321, a second amplifier 323 for secondarily amplifying a signal primarily amplified via the first amplifier 322, and an analog-digital converter 324 for converting a signal secondarily amplified via the second amplifier 323 into a digital signal.

The first light receiving element 321 receives light incident from the outside. At this point, the first light receiving element 321 may be implemented with a photodiode (PD) or a transistor (TR).

In addition, the first amplifier 322 converts a weak photocurrent detected by the first light receiving element 321 into a voltage and amplifies the voltage, which may be a trans impedance amplifier (TIA).

Further, the second amplifier 323 amplifies a voltage amplified via the first amplifier 322 to a voltage of sufficient magnitude to be processed by the analog-digital converter 324.

Furthermore, the analog-digital converter 324 converts an analog voltage to an equivalent digital voltage according to a specified sampling rate.

In addition, the second light receiving unit includes a second light receiving element 325 for receiving the incident light, a first amplifier 326 for primarily amplifying an optical signal incident via the second light receiving element 325, a second amplifier 327 for secondarily amplifying a signal primarily amplified via the first amplifier 326, and an analog-digital converter 328 for converting a signal secondarily amplified via the second amplifier 327 into a digital signal.

The control unit 330 performs substantially the same operation as the control unit 130 according to the first embodiment.

However, the control unit 330 detects the wearing state in response to the operation of the first light emitting unit and the first light receiving unit in a plurality of the light emitting units and the light receiving units in the wearing state detection mode.

In addition, in the human body signal detection mode, the control unit 330 detects a state of the human body (such as the heart rate) according to operations of the second light emitting unit and the second light receiving unit.

The human body wearable device according to the third embodiment may frequently detect the wearing state regardless of the detection of the human body state by using the first light emitting unit.

Further, although exemplary embodiments of the present disclosure have been illustrated and described above, the present disclosure is not limited to particular embodiments described above. One of ordinary skill in the art to which the present disclosure pertains should be able to modify and embody the present disclosure in various ways without departing from the gist of the present disclosure defined in the claims below, and the modified embodiments should not be understood as being separate from the technical spirit or prospect of the present disclosure.

The invention claimed is:

1. A human body wearable device, comprising:
a first light emitting unit configured to generate first light;
a second light emitting unit configured to generate second light;
a first light receiving unit configured to receive light incident from outside depending on an operation of the first light emitting unit;
a second light receiving unit configured to receive light incident from outside depending on operations of the second light emitting unit; and
a control unit configured to detect a wearing state of the human body wearable device in response to the operation of the first light emitting unit and an operation of the first light receiving unit in a wearing state detection mode, and to detect a state of the human body according to the operations of the second light emitting unit and an operation of the second light receiving unit in a human body signal detection mode,
wherein the control unit is also configured to
determine whether the human body wearable device is worn based on a difference value between a first intensity of the light incident on the first light receiving unit in an ON section of the first light emitting unit and that of the light incident on the first light receiving unit in an OFF section of the first light emitting unit while being in the wearing state detection mode, determine that the human body wearable device is not worn if the difference value is zero, while being in the wearing state detection mode,
determine that the human body wearable device is worn on a specific object if the difference value is greater than zero, while being in the wearing state detection mode,
detect a raw signal waveform of a pulse wave based on the first intensity if the human body wearable device is worn on the specific object, while being in the wearing state detection mode,
generate a waveform of a secondary differential signal by secondarily differentiating the detected raw signal waveform of the pulse wave while being in the wearing state detection mode,
generate a peak signal waveform by detecting a peak signal from the generated second-order differential signal waveform while being in the wearing state detection mode,
determine that the human body wearable device is worn on the human body if a heart rate (HR) of the peak signals of the generated peak signal waveform is within a range of 30 to 240 bpm, while being in the wearing state detection mode,
determine that the human body wearable device is worn on a thing if the heart rate (HR) exceeds the range of 30 to 240 bpm, and
enter the human body signal detection mode if the human body wearable device is worn on the human body,
detect a state of the human body according to the operations of the second light emitting unit and the second light receiving unit while being in the human body signal detection mode, and
detect whether the human body wearable device previously worn is separated from the human body in response to the operations of the first light emitting unit and the first light receiving unit while being in the human body signal detection mode.

2. A method of operating a human body wearable device, comprising:
entering a wearing state detection mode;
outputting a pulse signal including ON and OFF sections while being in the wearing state detection mode;
operating a first light emitter depending on the pulse signal while being in the wearing state detection mode;
determining whether the human body wearable device is worn based on a difference value between a first intensity of light incident on a first light receiving unit in an ON section of the first light emitting unit and that of light incident on the first light receiving unit in an OFF section of the first light emitting unit, while being in the wearing state detection mode,
determining that the human body wearable device is not worn if the difference value is zero, while being in the wearing state detection mode,
determining that the human body wearable device is worn on a specific object if the difference value is greater than zero, while being in the wearing state detection mode,
detecting a raw signal waveform of a pulse wave based on the first intensity if the human body wearable device is worn on a specific object, while being in the wearing state detection mode,
generating a waveform of a secondary differential signal by secondarily differentiating the detected raw signal waveform of the pulse wave while being in the wearing state detection mode,
generating a peak signal waveform by detecting a peak signal from the generated second-order differential signal waveform while being in the wearing state detection mode,
determining that the human body wearable device is worn on a human body if a heart rate (HR) of the peak signals of the generated peak signal waveform is within a range of 30 to 240 bpm, while being in the wearing state detection mode, determining that the human body wearable device is worn on a thing if the heart rate (HR) exceeds the range of 30 to 240 bpm, entering a human body signal detection mode if the human body wearable device is worn on the human body, detecting a state of the human body according to operations of a second light emitting unit and a second light receiving unit while being in the human body signal detection mode, and detecting whether the human body wearable device previously worn is separated from the human body in response to operations of the first light emitting unit and the first light receiving unit while being in the human body signal detection mode.

* * * * *